United States Patent
Warman

(10) Patent No.: US 11,298,548 B2
(45) Date of Patent: Apr. 12, 2022

(54) DUAL-ELECTROGRAM BASED CONTROL OF CARDIAC RESYNCHRONIZATION THERAPY

(71) Applicant: Medtronic, Inc., Minneapolis, MN (US)

(72) Inventor: Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 129 days.

(21) Appl. No.: 16/742,443

(22) Filed: Jan. 14, 2020

(65) Prior Publication Data

US 2020/0230420 A1    Jul. 23, 2020

Related U.S. Application Data

(60) Provisional application No. 62/795,723, filed on Jan. 23, 2019.

(51) Int. Cl.
| | |
|---|---|
| *A61N 1/368* | (2006.01) |
| *A61N 1/05* | (2006.01) |
| *A61N 1/365* | (2006.01) |

(52) U.S. Cl.
CPC ......... *A61N 1/36843* (2017.08); *A61N 1/056* (2013.01); *A61N 1/365* (2013.01)

(58) Field of Classification Search
None
See application file for complete search history.

(56) References Cited

U.S. PATENT DOCUMENTS

| | | | |
|---|---|---|---|
| 7,181,284 B2 | 2/2007 | Burnes et al. | |
| 2014/0257423 A1* | 9/2014 | Hedberg | A61N 1/3622 607/27 |
| 2018/0250514 A1 | 9/2018 | Ghosh | |
| 2018/0361162 A1 | 12/2018 | Ternes et al. | |

FOREIGN PATENT DOCUMENTS

| | | |
|---|---|---|
| WO | 2013109873 A1 | 7/2013 |
| WO | 2018209078 A1 | 11/2018 |

OTHER PUBLICATIONS (PCT/US2020/013799) International Search Report and the Written Opinion of the International Searching Authority, dated Apr. 30, 2020, 10 pages.

* cited by examiner

*Primary Examiner* — Brian T Gedeon
(74) *Attorney, Agent, or Firm* — Mueting Raasch Group

(57) ABSTRACT

In some examples, controlling delivery of CRT includes controlling an implantable medical device to deliver ventricular pacing according to a sequence of different values of a CRT parameter, and acquiring first and second electrograms from respective first and second electrode vectors. For each value of the CRT parameter, a value of a metric of comparison of a first activation interval between occurrences of a first fiducial of a cardiac cycle and a second fiducial of the cardiac cycle detected in the first electrogram to a second activation interval between occurrences of the first fiducial and the second fiducial detected in the second electrogram may be determined. A target value of the metric of comparison may be identified and an updated value of the CRT parameter determined based on the target value. The system then may control the IMD to deliver ventricular pacing at the updated value of the CRT parameter.

43 Claims, 7 Drawing Sheets

DUAL-ELECTROGRAM BASED CONTROL OF CARDIAC RESYNCHRONIZATION THERAPY

TECHNICAL FIELD

The disclosure relates generally to medical device systems and, more particularly, medical devices configured for cardiac resynchronization therapy.

BACKGROUND

Some types of implantable medical devices (IMDs), such as cardiac pacemakers or implantable cardioverter defibrillators, may be used to provide cardiac therapy to a patient via one or more electrodes. The cardiac therapy may be delivered to the heart in the form of pulses or shocks for pacing, cardioversion or defibrillation, or cardiac resynchronization therapy (CRT). CRT may help enhance cardiac output by resynchronizing the electromechanical activity of the ventricles of the heart in patients with conditions such as ventricular dyssynchrony. Some IMDs may sense intrinsic depolarizations of the heart and control the delivery of CRT to the heart based on the sensed intrinsic depolarizations.

SUMMARY

In general, this disclosure is directed to techniques for controlling the delivery of CRT by a medical device (e.g., an IMD) to a heart of a patient. The IMD may be controlled to deliver CRT to the heart at an updated (e.g., patient-specific) value of an CRT parameter that may be determined according to the techniques described herein.

As an example, a technique may include determining, by a medical device system including the IMD, an updated value of a CRT parameter based on an identified target value of at least one metric of comparison of a first activation interval to a second activation interval, such as a ratio of the longer of the first and second activation intervals to the shorter of the first and second activation intervals and/or a time difference between first and second activation intervals. In some examples, the CRT parameter may be an A-V time delay between activation of the right atrium (RA) and electrical stimulation of a ventricle, a V-V time delay between activation of one ventricle and electrical stimulation of the other ventricle, or another CRT parameter. The first and second activation intervals may be determined from first and second cardiac electrograms, respectively.

The target value may correspond to a target physiological response to CRT, such as fusion of ventricular activation during ventricular pacing. The first and second activation intervals may be intervals between the occurrence of first and second fiducials of a cardiac cycle. In some examples, an electrical activation time (e.g., a time of activation of a ventricle or a time of other local electrical activity of a portion of the heart) may be determined relative to the timing of another fiducial. One or both of the first and second fiducials of the cardiac cycle may be indicative of a global cardiac event, such as a timing of a contraction of a chamber of the heart, a timing of pacing of a chamber of the heart, or other such events. For example, one or both of the first and second fiducials of the cardiac cycle may be an onset of a QRS complex of the cardiac cycle, a peak of a QRS complex of the cardiac cycle (e.g., a minimum value, a minimum slope, or a maximum slope), a zero crossing, threshold crossing, or other aspect of a near or far-field EGM associated with the cardiac cycle, an onset of application of a pacing electrical stimulus, or the like, although any other suitable fiducial may be used.

One or both of the first and second fiducials of the cardiac cycle may be detected in first and second electrograms acquired from respective first and second electrode vectors. The first and second electrode vectors may be formed from a plurality of electrodes of a system that includes the IMD. In some examples, the first and second electrode vectors may be configured such that the first and second electrograms depict the cardiac cycle from two different perspectives relative to the heart.

Such a technique may include determining the target value based on the value of at least one metric of comparison of the first activation interval to the second activation interval determined for each value of a sequence of different values of a CRT parameter at which the IMD has delivered ventricular pacing, and identifying the target value from among the values of the at least one metric of comparison determined for the values of the sequence. Differences in the at least one metric of comparison that are associated with delivery of ventricular pacing at different values of the CRT parameter may correspond to differences in the rate of conduction of electrical impulses through the heart (e.g., the ventricles) resulting from ventricular pacing at the different values. In some examples in which a metric of comparison is at least one of a ratio of the first activation interval to the second activation interval and/or a time difference between the first and second activation intervals, the target value may be associated with a value of the CRT parameter at which a value of the time difference is at a minimum (or the ratio value is closest to 1), or at which a value of the time difference is equal to or less than a threshold value (or a value of the ratio is within a threshold distance from a value of 1). Such a value of the CRT parameter may result in improved conduction rate in patients with conduction dysfunction. Such a technique may further include determining the updated value of the CRT parameter, based on the identified target value of the CRT parameter, and controlling the IMD to deliver ventricular pacing at the updated value of the CRT parameter.

In some examples, the IMD may deliver CRT at the updated value of the CRT parameter until the expiration of a time period, until the medical device system determines a change in a physiological parameter (e.g., a heart rate and/or physical activity level) of the patient, or until the medical device system otherwise determines that further adjustment of values of one or more CRT parameters may be desirable. Upon expiration of a time period or determination of a change in a physiological parameter of a patient or other determination to adjust the value of the CRT parameter, the medical device system may determine new updated value of the CRT parameter and control the IMD to deliver CRT at the new updated value of the CRT parameter.

In some other example procedures, patient-specific values of a CRT parameter (e.g., an A-V or V-V delay) may be obtained from a visual examination of a cardiac electrogram during ventricular pacing, which may be done during or shortly after implantation of the CRT device or at another clinician visit. Thus, determination of a patient-specific value of a CRT parameter based on a visual examination of a cardiac electrogram may be limited to clinical or hospital settings. In such examples, CRT may be delivered according to the same value of the CRT parameter between clinician visits, which may be weeks or months apart. However, a patient-specific preferred value of the CRT parameter may change between clinician visits. In some examples, a patient-specific preferred value of the CRT parameter may change as the patient's disease state progresses (e.g., due to an acute heart failure (HF) decompensation event, deleterious tissue remodeling that occurs in the progression of HF, or otherwise during the course of HF treatment). Additionally, or alternatively, the patient-specific preferred value of the CRT parameter may change with changes in patient physical activity, when conduction properties of the heart may change due to activation of the sympathetic and parasympathetic nervous system. Since a preferred patient-specific value of a CRT parameter may change on a frequent basis (e.g., one or more times over the course of a day), similarly frequent updates to the value of a parameter by which CRT is delivered may be increase ventricular synchronization, which may improve patient outcome.

Accordingly, techniques described herein may provide periodic and/or as-needed adjustment of values of one or more CRT parameters. Such techniques may enable real-time adaptation of CRT to patient conditions, such as waking/sleeping, physical activity level, myocardial remodelling due to therapy, disease progression, and/or other conditions. Since the determination of an updated value of a CRT parameter according to the techniques described herein may be carried out by a medical device system including an IMD independently of clinician input or other interaction, the techniques described herein are not limited to clinical or hospital settings. Thus, the techniques described herein may enable more frequent determination of an updated value of CRT parameter than techniques for determining an updated value of a CRT parameter that rely upon clinician examination of the patient in which CRT may be delivered according to the same value of the CRT parameter between clinician visits (e.g., for weeks or months). In this manner, an updated, patient-specific value of a CRT parameter may be determined on a frequent basis, such as daily or even semi-continuously, which may provide improvements in ventricular synchronization over examples in which patient-specific values of CRT parameters are not determined or are determined less frequently such as only in a clinical setting.

In one example, a method for controlling delivery of cardiac resynchronization therapy (CRT) using an implantable medical device configured for implantation within a patient comprises, by processing circuitry of a medical device system comprising the implantable medical device: controlling the implantable medical device to deliver ventricular pacing to a heart of the patient according to a sequence of different values of a CRT parameter; acquiring, during the delivery of ventricular pacing according to the sequence, a first electrogram and a second electrogram from respective ones of a first vector formed from a plurality of electrodes of the medical device system and a second vector formed from the plurality of electrodes; determining, for each of the different values of the CRT parameter, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram; determining, for each of the different values of the CRT parameter, a value of a metric of comparison of the first activation interval to the second activation interval; identifying a target value of the metric of comparison of the first activation interval to the second activation interval; determining an updated value of the CRT parameter based on the identified target value; and controlling the implantable medical device to deliver the ventricular pacing at the updated value of the CRT parameter to provide CRT.

In another example, a system for controlling delivery of cardiac resynchronization therapy (CRT) to a patient comprises: a plurality of electrodes; an implantable medical device configured to deliver ventricular pacing to the patient; sensing circuitry configured to sense electrical activity of the heart via the plurality of electrodes; and processing circuitry configured to: control the implantable medical device to deliver ventricular pacing according to a sequence of different values of a CRT parameter; acquire, via the sensing circuitry and during the delivery of ventricular pacing according to the sequence, a first electrogram and a second electrogram from respective ones of a first vector formed from the plurality of electrodes and a second vector formed from the plurality of electrodes; determine, for each of the different values of the CRT parameter, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram; determine, for each of the different values of the CRT parameter, a value of a metric of comparison of the first activation interval to the second activation interval; identify a target value of the at least one of the ratio or the time difference; determine an updated value of the CRT parameter based on the identified target value; and control the implantable medical device to deliver the ventricular pacing the updated value of the CRT parameter to provide CRT.

In another example, a system for controlling delivery of cardiac resynchronization therapy (CRT) to a patient comprises: a plurality of electrodes; an implantable medical device configured to deliver ventricular pacing to the patient; sensing circuitry configured to sense electrical activity of the heart via the plurality of electrodes; and processing circuitry configured to: control the implantable medical device to deliver ventricular pacing according to a sequence of different values of an A-V delay; acquire, via the sensing circuitry and during the delivery of ventricular pacing according to the sequence, a first electrogram and a second electrogram from respective ones of a first vector formed from the plurality of electrodes and a second vector formed from the plurality of electrodes; determine, for each of the different values of the A-V delay, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram; determine, for each of the different values of the A-V delay, at least one of a ratio of the first activation interval and the second activation interval or a time difference between the first activation interval and the second activation interval; identify at least one of a minimum value of the time difference or a value of the ratio that is closest to a value of 1; determine an updated value of the A-V delay based on the identified at least one of the minimum value of the time delay or the value of the ratio that is closest to a value of 1; and control the implantable medical device to deliver the ventricular pacing the updated value of the A-V delay to provide CRT.

In another example, a non-transitory computer-readable medium storing instructions for causing processing circuitry to perform a method for controlling delivery of cardiac resynchronization therapy (CRT) using a medical device system, the medical device system comprising the processing circuitry, a plurality of electrodes, an implantable medical device configured for implantation within a patient and comprising at least one electrode of the plurality of electrodes, and sensing circuitry configured to sense electrical activity of the heart via the plurality of electrodes, comprises: controlling the implantable medical device to deliver ventricular pacing according to a sequence of different values of a CRT parameter; acquiring, during the delivery of ventricular pacing according to the sequence, a first electrogram and a second electrogram from respective ones of a first vector formed from the plurality of electrodes and a second vector formed from the plurality of electrodes; determining, for each of the different values of the CRT parameter, a first activation interval between an occurrence of a first fiducial of a cardiac cycle and a second fiducial of the cardiac cycle determined in the first electrogram and a second activation interval between the occurrence of the first fiducial of the cardiac cycle and the second fiducial of the cardiac cycle determined in the second electrogram; determining, for each of the different values of the CRT parameter, a value of a metric of comparison of the first activation interval to the second activation interval; identifying a target value of the metric of comparison of the first activation interval to the second activation interval; determining an updated value of the CRT parameter based on the identified target value; and controlling the implantable medical device to deliver the ventricular pacing at the updated value of the CRT parameter to provide CRT.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Figure 1:
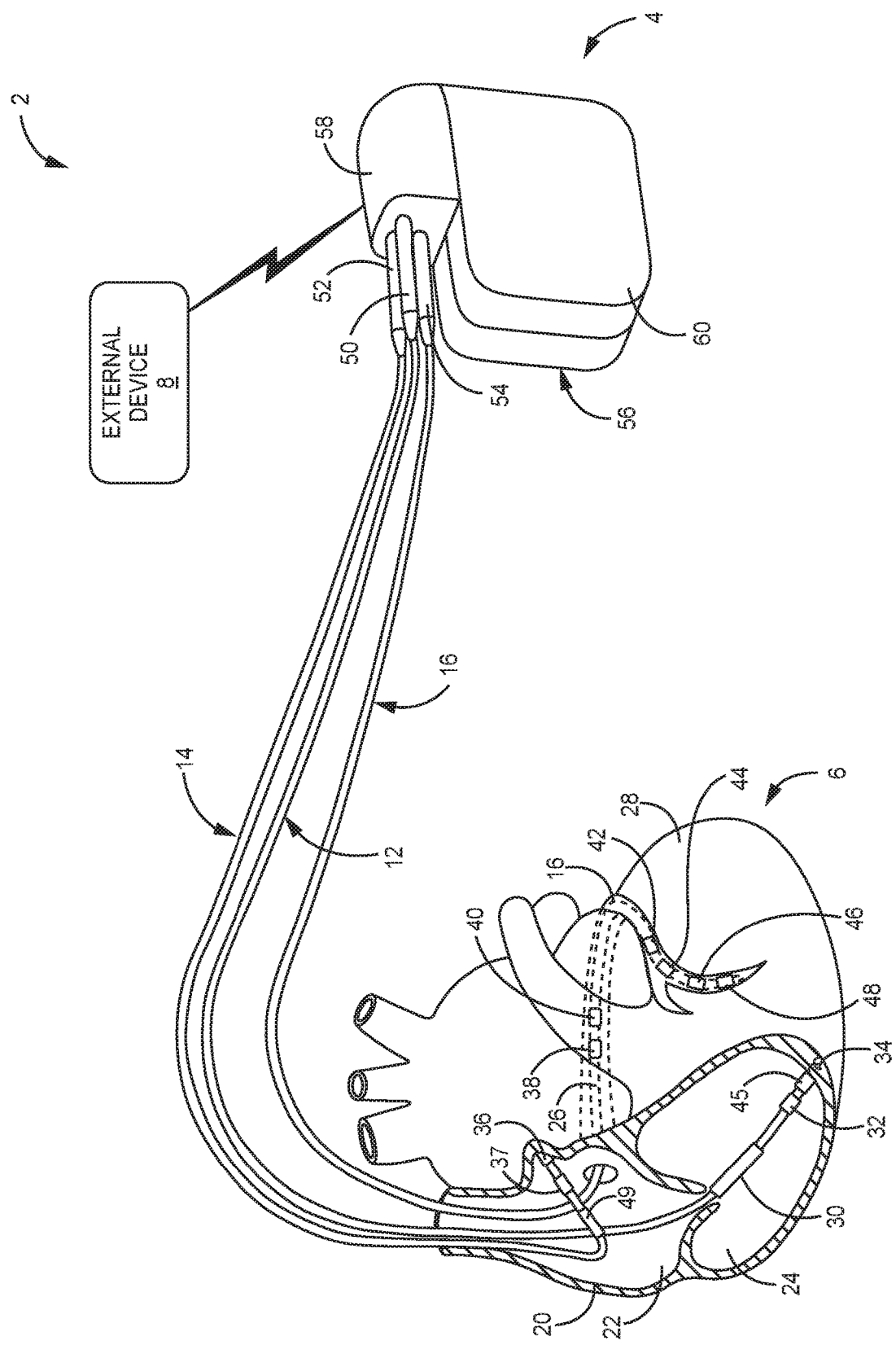
FIG. 1 is a conceptual drawing illustrating an example of a medical device system including an implantable medical device and an external device in conjunction with a patient's heart.

In general, this disclosure describes example techniques and systems related to controlling the delivery of CRT by an IMD to a patient according to an updated value of a CRT parameter. Processing circuitry of the IMD or a system that includes the IMD may control the IMD to deliver ventricular pacing to a heart of the patient according to a sequence of different values of a CRT parameter (e.g., an A-V or V-V delay). For example, during delivery of CRT, the processing circuitry may determine that a current period of time has elapsed or that an event indicating a change in patient status has occurred and enter a testing phase to determine an updated value of a CRT parameter.

During the delivery of ventricular pacing according to the sequence, the processing circuitry may acquire a first cardiac electrogram and a second cardiac electrogram from respective ones of a first vector formed from a plurality of electrodes of the medical device system and a second vector formed from the plurality of electrodes. In some examples, the plurality of electrodes from which the first and second vectors are formed may be electrodes that are not used in the delivery of CRT by the IMD, although in other examples one or more electrodes may be commonly used in the first or second vector and in the delivery of CRT.

In some examples, the processing circuitry may acquire a first electrogram from a first electrode vector by subtracting signals from two component vectors including at least one common electrode, e.g., a signal from a vector including at least one electrode on a first lead from a signal from another vector including at least one electrode on a second lead. The processing circuitry may similarly acquire a second electrogram from a second electrode vector by subtracting a signal from a vector including the same at least one electrode on the first lead from a vector including at least one electrode on the second lead different from the at least one electrode on the second lead used in acquiring the first electrogram. In other examples, the processing circuitry may acquire the first and second electrograms from other combinations of electrodes on leads of a medical device system and/or a housing electrode. In any such examples, a signal from at least one electrode on a lead may be a single signal received from two or more physically distinct electrodes on the lead, or a single electrode on the lead in combination with a housing electrode of a housing of the IMD or other indifferent electrode.

In any such examples, the first and second electrograms acquired from the first and second electrode vectors may illustrate cardiac activity from two distinct perspectives relative to the heart. For example, the first and second electrode vectors may be substantially orthogonal to one another. As further discussed below, the different perspectives of cardiac activity illustrated by the first and second electrograms may help enable the processing circuitry to determine whether ventricular pacing delivered by the IMD according to a value of a CRT parameter is associated with a target outcome of CRT (e.g., fusion between left ventricular activation and right ventricular activation).

The processing circuitry then may determine, for each of the different values of the CRT parameter, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram.

The first and second fiducials may correspond to features of the cardiac cycle. In some examples, the first fiducial may correspond to a time at which the IMD delivers a pacing pulse, which may appear in an electrogram as a pacing spike. A pacing spike may be a spike in electrogram amplitude corresponding to delivery of a pacing pulse (e.g., a ventricular pacing pulse) to the heart during the cardiac cycle. In the example of ventricular pacing, the processing circuitry may control the IMD to deliver the pacing pulse following atrial activation and prior to intrinsic ventricular activation. Thus, in such examples, the pacing spike may appear in the first and second electrograms between a P-wave and a QRS complex of the cardiac cycle. Examples in which a pacing spike may be detected may include examples in which one medical device (e.g., a medical device implanted within or external to the patient) is used to sense cardiac electrical signals according to the techniques described herein and another medical device is used to deliver ventricular pacing. In examples in which a pacing spike is detected, the pacing spike may be detected and distinguished from intrinsic cardiac electrical activity based on one or more criteria (e.g., amplitude and/or slew rate), each of which may be expected to be greater than that of intrinsic cardiac signals.

Although the techniques herein may include detection of a pacing spike, in some examples processing circuitry may otherwise determine the timing of the pacing pulse, e.g., based on the time at which the processing circuitry controlled the IMD to deliver the pacing pulse, as further discussed below. In some examples, the second fiducial may correspond to a feature of the electrogram related to depolarization of the heart in response to the pacing pulse, such as one of an onset of a paced ventricular activation in the electrogram, a maximum of the first derivative of the electrogram (dv/dt), a detected R-wave in the electrogram, or a maximum amplitude of the electrogram.

In some examples, the processing circuitry may determine the first and second activation intervals by detecting both the first fiducial of a cardiac cycle and the second fiducial of a cardiac cycle in respective ones of the first and second electrograms. However, in other examples, the processing circuitry may determine an activation interval by detecting one of first and second fiducials (e.g., the second fiducial) of a cardiac cycle in an electrogram and determining a time of the other fiducial (e.g., the first fiducial) of the cardiac cycle in a different manner. For example, the processing circuitry may determine a time of an occurrence of the first fiducial based on a time at which the IMD delivers a pacing pulse instead of detecting the first fiducial in the first and second electrograms. In such examples, the time at which the IMD delivers the pacing pulse may be "known" to timing and/or control aspects of the processing circuitry. Thus, the determination of a time of an occurrence of the first fiducial of a cardiac cycle is not necessarily dependent upon signal detection from an electrode vector and analysis of an electrogram, which in some examples may simplify and/or enhance the accuracy of the determination of the first and second activation intervals by the processing circuitry.

The processing circuitry may determine, for each value of the sequence of different values of the CRT parameter by which an IMD delivers ventricular pacing, a relationship between the first activation interval and the second activation interval. The relationship between the first activation interval and the second activation interval may be described herein as at least one metric of comparison of the first activation interval to the second activation interval. In some examples, the at least one metric of comparison may be at least one of a ratio between the first and second activation intervals (e.g., a ratio of the time duration of longer of the first and second activation intervals to the time duration of the shorter of the first and second activation intervals), a time difference between the first and second activation intervals, and/or one or more other suitable metrics. In some examples, the time difference between the first and second activation intervals may be a time difference between the occurrence of the second fiducial of the cardiac cycle detected in the first electrogram and the occurrence of the second fiducial of the cardiac cycle detected in the second electrogram. The processing circuitry then may identify a target value of the at least one metric of comparison from the values of the metric of comparison associated with the different values of the CRT parameter.

The processing circuitry may identify the target value by identifying a minimum value of the time difference (or the ratio value closest to 1), or a value of the time difference that is equal to or less than a threshold value (or a value of the ratio that is within a threshold distance from a value of 1). That is, the target value of a metric of comparison may be associated with a value of the CRT parameter of the sequence at which delivery of ventricular pacing results in a maximum or threshold degree of temporal similarity between a first activation interval detected in a first electrogram and a second activation interval detected in a second electrogram.

The degree of temporal similarity between the first and second activation intervals may be associated with a rate of conduction of electrical impulses through the heart (e.g., the ventricles). In some examples, a patient with a conduction dysfunction may experience an interventricular conduction defect, such as left bundle branch block (LBBB) and/or right bundle branch block (RBBB). In LBBB and RBBB, electrical impulses are not conducted in a normal fashion along the respective right or left bundle branch. Thus, in patients with bundle branch block, the activation of either the RV or LV is delayed with respect to the other ventricle, causing asynchrony between the depolarization of the right and left ventricles. Ventricular asynchrony may be identified by a widened QRS complex (e.g. greater than or equal to about 120 ms) due to the increased time for the activation to traverse the ventricular conduction paths. With respect to some examples described herein, a widened QRS complex or other indication of a conduction dysfunction may be more apparent in the second electrogram than in the first electrogram. For example, the second electrode vector from which the processing circuitry acquires the second electrogram may include an electrode positioned further from the electrodes by which the IMD delivers ventricular pacing than the electrodes of the first electrode vector.

In examples in which the patient is experiencing a conduction dysfunction, an electrical impulse may take longer to reach such an electrode of the second electrode vector than examples in which the patient is experiencing a lesser degree of conduction dysfunction or no conduction dysfunction. Thus, in examples in which the patient is experiencing the conduction dysfunction, the value of at least one metric of comparison, such as a ratio of the longer of the first and second activation intervals to the shorter of the first and second activation intervals and/or a time difference between the first activation interval and the second activation interval may be greater than examples in which the patient is experiencing a lesser degree of conduction dysfunction or no conduction dysfunction. Ventricular pacing delivered by the IMD may help reduce conduction dysfunction by restoring synchronous depolarization and contraction of one or more chambers of the heart, which may reduce the value of the ratio of the longer of the first and second activation intervals to the shorter of the first and second activation intervals and/or time difference between the first activation interval and the second activation interval. A minimum value of the time difference (or the ratio value closest to 1), or a value of the time difference that is equal to or less than a threshold value (or a value of the ratio that is within a threshold distance from a value of 1) resulting from delivery of ventricular pacing at a value of a CRT parameter, relative to other values of the CRT parameter of the sequence, may be associated with a target outcome of ventricular pacing such as fusion of ventricular activation. Thus, the target value desirably may be a minimum value of the time difference (or the ratio value closest to 1), or a value of the time difference that is equal to or less than a threshold value (or a value of the ratio that is within a threshold distance from a value of 1).

In any such examples, the target value of a metric of comparison may be associated with a value of a CRT parameter that enhances or optimizes patient hemodynamic response relative to one or more other different values of the CRT parameter of the sequence. For example, the target value of a metric of comparison may be associated with a value of the CRT parameter at which ventricular pacing results in a target outcome, such as fusion between left ventricular activation and right ventricular activation. Thus, the processing circuitry may determine the updated value of the CRT parameter based on the identified target value of the metric of comparison. After determining the updated value of the CRT parameter, the processing circuitry may control the IMD to deliver the ventricular pacing at the updated value of the CRT parameter to provide CRT, such as by controlling the IMD to deliver the ventricular pacing at the value of the CRT parameter that resulted in the target value.

In some examples, the CRT parameter is an A-V delay, which may be a delay between atrial activation and delivery of a pacing pulse by the IMD to a ventricle (e.g., the left ventricle). In such examples, the processing circuitry may control the IMD to deliver the ventricular pacing according to the sequence of different values of the A-V delay by controlling the IMD to deliver left-ventricular pacing according to the sequence of different values of A-LV delay, and may control the IMD to deliver the ventricular pacing at the updated value of the CRT parameter by controlling the IMD to deliver LV fusion pacing. For example, the processing circuitry may control the IMD to deliver the ventricular pacing the updated value of the CRT parameter by controlling the IMD to deliver the ventricular pacing at the value of the CRT parameter that resulted in the target value. In addition, although a CRT parameter may be described herein as being an A-V delay with respect to some example techniques, such techniques may be adapted to determining values of other CRT parameters, such as values of a V-V delay or others.

In any such examples, the processing circuitry may control the IMD to deliver CRT at the updated value of the CRT parameter until the expiration of a time period, until medical device system determines that a physiological parameter (e.g., a heart rate and/or physical activity level) of the patient has changed, and/or until the processing circuitry otherwise determines that further adjustment of values of one or more CRT parameters may be desirable, such as upon receiving input from an external device requesting an updated value of the CRT parameter. Thus, techniques described herein may enable the frequent or substantially real-time adaptation of CRT to meet an individual patient's changing needs. In some examples, controlling the IMD to deliver CRT at a patient-specific value of the CRT parameter may increase hemodynamic benefits of CRT, and/or may improve a clinical response of the patient. For example, symptoms experienced by a patient who otherwise is non-responsive to CRT may be improved by controlling an IMD to deliver CRT at a patient specific value of a CRT parameter.

In some examples, the IMD may be an implantable CRT device that includes the processing circuitry. Some example medical device systems including the implantable CRT device (e.g. CRT-D, CRT-P) may include one or more implantable leads, which configured for implantation within the patient, each of which may include one or more electrodes of the plurality of electrodes from which the first and second electrode vectors may be formed. In some such examples, the implantable CRT device may be coupled to the plurality of electrodes by the one or more implantable leads.

In some such examples, the implantable CRT device may include a housing. The housing may include an electrode of the plurality of electrodes. The one more implantable leads may include a first lead configured for implantation within a right ventricle of the heart and a second lead configured for implantation within a left ventricle of the heart. In some examples, the first electrode vector may be between the housing and an electrode of the plurality of electrodes on the first lead, and the second vector may be formed between an electrode of the plurality of electrodes on the first lead and an electrode of the plurality of electrodes on the second lead.

In some examples, a medical device system including an IMD includes a memory. In some such examples, processing circuitry of the medical device system may be configured to control the IMD to deliver the ventricular pacing to the heart of the patient according to a sequence of different values of a CRT parameter by at least controlling the IMD to deliver the ventricular pacing to the heart of the patient according to the sequence of different values of the CRT parameter based on a determination to update one or more CRT parameters. The one or more CRT parameters may include the CRT parameter, and the processing circuitry may be further configured to store the updated CRT parameter in the memory as at least one updated value of the one or more CRT parameters.

Although a patient-specific value of a CRT parameter may be obtained from a visual examination of a cardiac electrogram during ventricular pacing in some other techniques, as noted above, determination of a patient-specific value of a CRT parameter based on a visual examination of a cardiac electrogram may be limited to clinical or hospital settings, and thus may be updated only infrequently. Other techniques that may be used to determine patient-specific values of CRT parameters, such as echocardiographic techniques, also may be complicated and the measurements resulting therefrom may be inaccurate. A further limitation of echocardiographic optimization is that it is performed with the patient in the recumbent position in full rest, even though CRT delivered according to patient-specific values of CRT parameters may be more beneficial under conditions of greater physical activity.

Overall, other techniques that may be used to determine patient-specific values of a CRT parameter (e.g., A-V or V-V delay), such as different echocardiographic measures, invasive hemodynamic measures (dP/dt, stroke work), finger photoplethysmography, or peak endocardial acceleration, may be time and resource consuming and/or may be subject to large measurement variability. Moreover, most such measurements typically are performed during in-office visits, and although some clinical trials of CRT have incorporated some manner of AV-delay determination, definitive data supporting their superiority over an empiric A-V delay are lacking. These factors and/or other factors many prompt clinicians to leave CRT device settings at the default values (i.e., "out-of-the-box" values), instead of determining patient-specific values of CRT parameters for individual patients. Thus, in such other techniques, patient-specific values of one or more CRT parameters may be determined infrequently, if at all.

The techniques described herein may enable ongoing (e.g., periodic or substantially continuous), ambulatory determination of patient-specific values of one or more CRT parameters (e.g., an A-V delay or V-V delay) based on first and second electrograms acquired from first and second electrode vectors formed from a plurality of electrodes, instead of infrequent determinations of a patient-specific value of a CRT parameter made in a clinician's office or hospital. In some examples, the techniques described herein may improve acute hemodynamic benefits of CRT, such as by up to 20-30%, and/or may improve short-term clinical response. In some examples, such an improvement in hemodynamic benefit and/or short-term clinical response may improve symptoms in patients who otherwise do not obtain significant clinical benefit from CRT.

In some examples in which a CRT parameter is an A-V delay, a value of the A-V delay by which the IMD delivers ventricular pacing may be periodically updated to provide more efficient pacing and/or improve hemodynamic response of the patient to CRT, such as upon expiration of a time period or determination of a change in a physiological parameter of a patient or other determination to adjust the value of the A-V delay. Fusion pacing and biventricular pacing are described in further detail below. While the pacing stimuli may be pacing pulses or continuous time signals, the pacing stimuli are primarily referred to herein as pacing pulses for ease of description.

Fusion-based CRT, also referred to herein as fusion pacing, may be useful for restoring a depolarization sequence of a heart of a patient, which may be irregular due to ventricular dysfunction, in patients with preserved intrinsic atrial-ventricular (AV) conduction. Adequate fusion of ventricular action may restore a depolarization sequence of the heart by synchronizing the activation of the ventricles, thereby increasing the systolic pressure or the maximal rate of pressure increase (LVdP/dtmax) of the paced ventricle. In a fusion pacing configuration, the IMD delivers one or more fusion pacing pulses to one of the ventricles, and not the other. For example, the IMD may deliver one or more fusion pacing pulses to a later-contracting ventricle (V2) in order to pre-excite the V2 and synchronize the depolarization of the V2 with the depolarization of the earlier contracting ventricle (V1). The ventricular activation of the V2 may "fuse" or "merge" with the ventricular activation of the V1 that is attributable to intrinsic conduction of the heart. In this manner, the intrinsic and pacing-induced excitation wave fronts may fuse together such that the depolarization of the V2 is resynchronized with the depolarization of the V1. In some examples, the ventricular activation of the V2 may be considered to be "fused" or "merged" with the ventricular activation of the V1 when, for example, a value of LVdP/dt or other measure of contractility is greater than a corresponding threshold value or when a far-field QRS width is less than a corresponding threshold value.

The IMD may be configured to deliver the fusion pacing pulse to the V2 according to a fusion pacing interval. The fusion pacing interval specifies a delay between an atrial pace or sense event and delivery by the IMD of a fusion pacing pulse to the V2. In some examples, an atrial sense event may be a P-wave of a sensed electrical cardiac signal and an atrial pacing event may be, for example, the time at which a stimulus is delivered to the atrium.

In some examples, the right ventricle (RV) may be the V1 and the left ventricle (LV) may be the V2. In other examples, the LV may be the V1 while the RV may be the V2. Although the first-depolarizing ventricle V1 is described as being the RV and the later-depolarizing ventricle V2 is described as being the LV with respect to some examples described herein, the first-depolarizing ventricle V1 instead may be the LV and the later-depolarizing ventricle V2 instead may be the RV in any such examples.

In some fusion pacing techniques, the IMD may deliver a pacing pulse to the V2 ($V2_P$) upon expiration of a fusion pacing interval. The processing circuitry may determine the fusion pacing interval based on sensed intrinsic depolarization of the V1 (e.g., sensed ventricular activation ($V1_S$)). Ventricular activation may be indicated by, for example, an R-wave of a sensed electrical cardiac signal. An example of a fusion pacing technique that times the delivery of the V2 pacing pulse ($V2_P$) to the intrinsic depolarization of the V1 is described in U.S. Pat. No. 7,181,284 to Burnes et al., which is entitled, "APPARATUS AND METHODS OF ENERGY EFFICIENT, ATRIAL-BASED BI-VENTRICULAR FUSION-PACING," and issued on Feb. 20, 2007. U.S. Pat. No. 7,181,284 to Burnes et al. is incorporated herein by reference in its entirety.

In one example disclosed by U.S. Pat. No. 7,181,284 to Burnes et al., a pacing pulse to the V2 ($V2_P$) is delivered a predetermined period of time following an atrial pace or sense event ($A_{P/S}$), where the predetermined period of time is substantially equal to the duration of time between the atrial pace or sense event ($A_{P/S}$) and a V1 sensing event ($V1_S$) of at least one prior cardiac cycle decremented by a duration of time referred to as the pre-excitation interval (PEI). Thus, one example equation that may be used to determine a fusion pacing interval ($A_{P/S}$–$V2_P$):

$$A_{P/S}-V2_P=(A_{P/S}-V1_S)-\text{PEI} \quad \text{Equation (1)}$$

A cardiac cycle may include, for example, the time between the beginning of one heart beat to the next heartbeat, as further discussed below with respect to FIGS. 3A and 3B. The duration of time between the atrial pace or sense event ($A_{P/S}$) and a V1 sensing event ($V1_S$) may be, for example, a measurement of intrinsic AV conduction time from an atrium to the first contracting ventricle of the heart of the patient. The PEI may indicate the amount of time with which a V2 pacing pulse precedes a V1 sensing event in order to achieve the fusing of the electromechanical performance of the V1 and V2 (e.g., the latency of activation of V2). That is, the PEI may indicate the amount of time from the delivery of the V2 pacing pulse that may be required to pre-excite the V2, such that the electromechanical performance of V1 and V2 merge into a fusion event. In some examples, the PEI is automatically determined by a medical device delivering the pacing therapy, e.g., based on determined intrinsic conduction times, while in other examples, the PEI may be predetermined by a clinician. In some examples, the PEI is a programmed value (e.g., about one millisecond (ms) to about 250 ms or more, such as about 100 ms to about 200 ms, or about 10 ms to about 40 ms) or is an adaptive value, such as about 10% of a measured intrinsic A-V2 conduction interval or measured intrinsic A-A cycle length.

The magnitude of the PEI may differ based on various factors, such as the heart rate of the patient, a dynamic physiologic conduction status of the heart of the patient, which may change based upon the physiological condition of the patient (e.g., ischemia status, myocardial infarction status, and so forth), as well as factors related to the therapy system, such as the location of sensing electrodes of the leads of the therapy system, the location of the pacing electrodes of the therapy system, and internal circuitry processing delays of the medical device.

In some other example techniques for determining an appropriate A-V delay by which to deliver CRT, such as those that directly measure an A-V interval in the absence of pacing, the appropriate A-V delay may have to account for the PEI as shown above. In contrast, to determine an appropriate A-V delay according to the techniques described herein, e.g., using a D-VCG, pacing is performed, and the paced A-V delay is sequentially changed, e.g., prolonged, to detect the onset of intrinsic non-paced ventricle contribution. Detection of the onset of intrinsic non-paced ventricle contribution in this manner is based on actual measured changes in activation and not on predicted values. In this manner, the techniques described herein may directly measure the moment of fusion, whether LV latency is present or not The techniques described herein also may be used in the selection of appropriate locations for the pacing electrodes used to deliver CRT. During an example technique that includes controlling the IMD to deliver ventricular pacing to a heart according to a sequence of different values of a CRT parameter and acquiring the first and second electrograms from the first and second electrode vectors, it may be preferred to control the IMD to deliver the ventricular pacing using different electrodes than the electrodes that form the first and second electrode vectors. In some examples in which the IMD includes defibrillation capabilities, one or more of the electrodes that form the first and second electrode vectors may be defibrillation electrodes. In some examples, a clinician may be able to select which electrodes are employed to perform the various functions described with respect to an example medical device system (e.g., pacing, acquiring electrograms, and/or defibrillation) if a sufficient number of electrodes are available. For example, during initial implant of the IMD, the clinician may control the IMD to deliver ventricular pacing while moving one or more pacing electrodes to different locations. Based upon the results, the clinician may choose a preferred set of locations for initial implantation of the electrodes.

In some examples, combinations of electrodes by which the IMD may deliver ventricular pacing and/or sense electrical signals may be selectable post-implantation. In such examples, a clinician may select pacing and/or sensing electrode configuration of the medical device system and input the selected pacing configuration into an external user device, such as a remote computer. In other examples, the IMD may periodically test available pacing and/or sensing electrode configurations. In such examples, the processing circuitry may control the IMD to transmit recommended pacing and/or sensing electrode configurations to an external user device or automatically select a preferred configuration.

In some examples, the techniques described herein may enable more accurate data collection from an individual patient, as average data from multiple patients is not necessarily relied upon for updating a value of a CRT parameter in such examples. In any such examples, techniques described herein may enable substantially-continuous adaption of values of CRT parameters to changes in patient physiological functions such as varying levels of physical activity, waking/sleeping, worsening or improving cardiac function, or other changes in patient physiological function.

Figure 2:
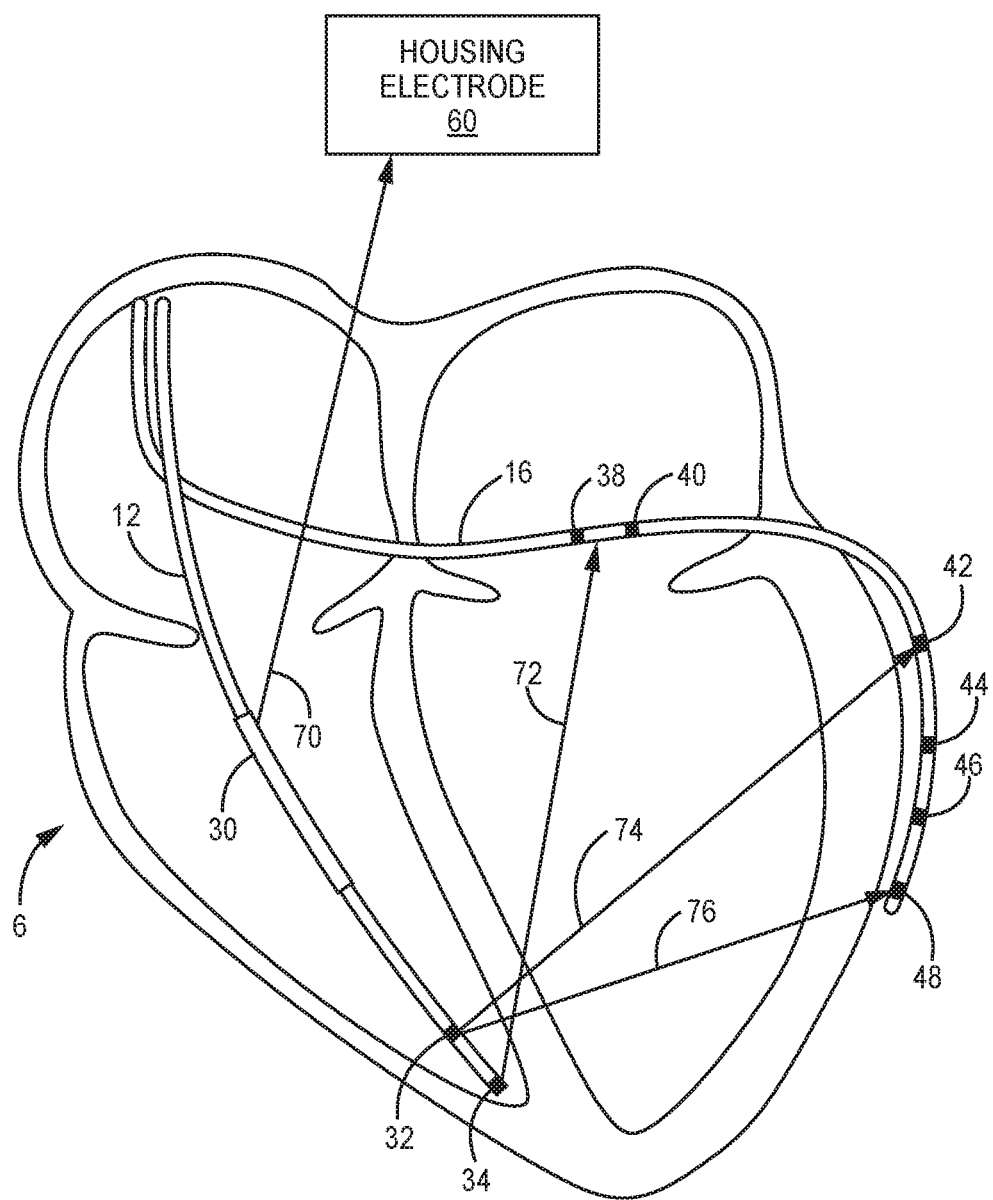
FIG. 2 is a conceptual drawing illustrating portions of the implantable medical device of FIG. 1 in conjunction with the patient's heart and electrograms that may be acquired using the medical device system of FIG. 1.

FIGS. 1 and 2 illustrate components of example medical device system 2 for controlling an IMD 4 to deliver CRT to a heart 6 of a patient (not shown), in accordance with the example techniques described herein.

FIG. 1 is a conceptual drawing illustrating an example of medical device system 2, including IMD 4 and an external device 8, in conjunction with heart 6. Medical device system 2, which includes IMD 4 and external device 8, is an example of a medical device system configured to implement the example techniques described herein for controlling the delivery of CRT to heart 6 of the patient. In some examples, IMD 4 may be an implanted, multi-channel cardiac pacemaker, implantable cardioverter-defibrillator (ICD), implantable pulse generator (IPG), leadless (e.g., intracardiac) pacemaker, extravascular pacemaker and/or ICD, or other IMD or combination of such IMDs configured to deliver CRT to heart 6.

In some examples, IMD 4 may be configured to sense electrical signals corresponding to the depolarization and repolarization of heart 6, e.g., a cardiac electrogram (EGM), via electrodes on one or more leads 12, 14, and 16 or the housing of IMD 4. Additionally, or alternatively, IMD 4 may sense electrical signals corresponding to the depolarization and repolarization of heart 6 via extravascular electrodes (e.g., electrodes positioned outside the vasculature of the patient), such as epicardial electrodes, external surface electrodes, subcutaneous electrodes, and the like. In any such examples, the configurations of electrodes used by IMD 4 for sensing and pacing may be unipolar or bipolar. In some examples, system 2 may determine heart rate to, e.g., detect arrhythmia, based on the electrical signals sensed via the electrodes. IMD 4 may also deliver therapy in the form of electrical signals to heart 6 via electrodes located on one or more leads 12, 14, and 16 or a housing of IMD 4. In the illustrated example, IMD 4 is connected to leads 12, 14 and 16, and may be communicatively coupled to external device 8.

Leads 12, 14, and 16 extend into heart 6 of the patient to sense electrical activity of heart 6 and to deliver electrical stimulation to heart 6. In the example shown in FIG. 1, RV lead 12 extends through one or more veins (not shown), vena cava 20, RA 22, and into RV 24 for sensing right ventricular cardiac signals and delivering pacing or shocking pulses to RV 24. Right atrial lead 14 extends through one or more veins and vena cava 20 and is positioned such that a distal end of LV lead 16 is in the vicinity of RA 22 and vena cava 20 for sensing right atrial cardiac signals and delivering pacing or shocking pulses to RA 22. LV lead 16 extends through one or more veins, vena cava 20, RA 22, and into coronary sinus 26 (illustrated in phantom) to a region adjacent to the free wall of LV 28 of heart 6. In some examples, electrodes of lead 16 may be used in combination with electrodes of lead 12 and/or lead 14 for delivering electrical shocks for cardioversion and defibrillation therapies. In other examples, lead 16 may also be equipped with a distal tip electrode and ring electrode for pacing and sensing functions in the left chambers of heart 6.

In the illustrated example, lead 12 includes bipolar electrodes 32 and 34, which may be located adjacent to a distal end of lead 12. Lead 14 includes bipolar electrodes 36 and 37, which may be located adjacent to a distal end of lead 14. Lead 16 may be a multipolar LV lead and may include electrodes 38 and 40, and electrodes 42, 44, 46, and 48. In some examples, electrodes 42, 44, 46, and 48 may be located adjacent to a distal end of lead 16, as illustrated in FIG. 1. In some examples, electrodes 38, 40, 42, 44, 46, and/or 48 of lead 16 may be segmented electrodes having a plurality of discrete electrodes arranged at respective circumferential positions around the circumference of lead 16.

Electrodes 34 and/or 36 may be extendable helix tip electrodes and may be mounted retractably within respective insulative electrode heads. For example, electrode 34 may be mounted retractably within insulative electrode head 45 positioned on lead 12 and electrode 36 may be mounted retractably within an insulative electrode head positioned on lead 14 (not shown), respectively. In some examples, one or both of leads 12 and 14 may also include one or more elongated coil electrodes, such as coil electrode 30 of lead 12 and/or a coil electrode 49 of lead 14. In some examples, electrodes 30-49 of leads 12, 14, and 16 may be electrically coupled to a respective conductor within a lead body of a corresponding one of leads 12, 14, and 16, and thereby coupled to circuitry within IMD 4.

In some examples, leads 12, 14, and 16 respectively include in-line connectors 50, 52, and 54. IMD 4 may further include an IPG 56, which may include a connector block 58 and a hermetically-sealed housing 60. In-line connectors 50, 52, and 54 may be configured to fit into corresponding bipolar bores of connector block 58, which may be coupled to electrically insulated conductors within leads 12, 14, and 16, thereby connecting electrodes 30-49 to IPG 56.

In some examples, one or more outward-facing portions of housing 60 may be uninsulated, and thus may enable housing 60 to be used as a housing electrode. In some examples, substantially all of housing 60 may be uninsulated, such that substantially all of housing 60 defines the housing electrode. In some other examples, housing 60 may define one or more additional housing electrodes (not shown), which may be defined by corresponding divisions between insulated and uninsulated portions of housing 60.

In some examples, IMD 4 may be configured for bipolar sensing of electrical signals corresponding to a cardiac electrogram of heart 6 via any bipolar combination of electrodes 30-49. In other examples, IMD 4 may be configured for unipolar sensing of electrical signals corresponding to a cardiac electrogram of heart 6 via any one of electrodes 30-49 in combination with housing electrode 60. In any such examples, IMD 4 may be configured to deliver CRT to heart 6 via any combination of electrodes 30-49.

In some examples, as part of CRT delivered to heart 6, IMD 4 may be configured to deliver at least one of fusion pacing or biventricular pacing to heart 6. In some examples of fusion pacing, IMD 4 may deliver a pacing stimulus (e.g., a pacing pulse) LV 28 of heart 6, where the pacing stimulus is timed such that an evoked depolarization of LV 28 is fused with the intrinsic depolarization of RV 24, resulting in a ventricular resynchronization. In this manner, a pacing pulse delivered to LV 28 may pre-excite LV 28 in examples in which LV 28 is conduction delayed and may help fuse the activation of LV 28 with the activation of RV 24 from intrinsic conduction. The fusion of the depolarization of LV 28 and RV 24 may result in synchronous activation and contraction of LV 28 with RV 24. In examples described herein, the fusion pacing configuration may be referred to as "left-ventricular" pacing. However, it should be understood that a fusion pacing configuration may include right-ventricular pacing in any of the examples described. In some examples in which IMD 4 is in a biventricular-pacing configuration, IMD 4 may deliver a pacing stimulus (e.g., a pacing pulse) to RV 24 and a pacing stimulus to LV 28 in a manner that synchronizes activation and contraction of LV 28 and RV 24, e.g., based on a selected or determined V-V delay.

CRT provided by IMD 4 may be useful for maintaining a cardiac rhythm in some examples in which the patient has a conduction dysfunction (e.g., a dysfunction in which the natural electrical activation system of heart 6 is disrupted). The natural electrical activation system of a human heart (e.g., heart 6) involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of RA 22. The depolarization wave is transmitted through the atrial conduction pathways of Bachmann's Bundle and the Internodal Tracts at the atrial level into the septum of the left atrium (LA; not shown). When the atrial depolarization wave has reached the AV node, the atrial septum, and the furthest walls of the right and left atria, the atria may contract as a result of the electrical activation. The aggregate right atrial and left atrial depolarization wave appears as the P-wave of the PQRST complex of an electrical cardiac signal, such as in first and second electrograms acquired by processing circuitry of system 2 (e.g., processing circuitry of IMD 4) from corresponding first and second electrode vectors. For example, when the amplitude of the atrial depolarization wave passing between a pair of unipolar or bipolar pace/sense electrodes located in or adjacent RA 22 and/or the LA exceeds a threshold, the processing circuitry may detect a sensed P-wave. The sensed P-wave may also be referred to as an atrial sensing event, or an RA sensing event (RAS). A P-wave sensed in the LA may be referred to as an atrial sensing event or an LA sensing event (LAS).

During or after the atrial contractions, the AV node distributes the depolarization wave inferiorly down the Bundle of His in the intraventricular septum. The depolarization wave may travel to the apical region of heart 6 and then superiorly though the Purkinje Fiber network. The aggregate right ventricular and left ventricular depolarization wave and the subsequent T-wave accompanying re-polarization of the depolarized myocardium may appear as the QRST portion of the PQRST cardiac cycle complex. When the amplitude of the QRS ventricular depolarization wave passing between a bipolar or unipolar pace/sense electrode pair located on or adjacent LV 28 or RV 24 exceeds a threshold, it may be detected by IMD 4 as a sensed R-wave. The sensed R-wave may also be referred to as a ventricular sensing event, an RV sensing event (RVS), or an LV sensing event (LVS), depending upon which ventricle is being sensed by electrodes of system 2 in a particular example. In some examples, the sensed R-wave may be a second fiducial of a cardiac cycle that processing circuitry of system 2 may detect in first and second cardiac electrograms acquired by the processing circuitry during delivery of ventricular pacing by IMD 4.

Some patients, such as patients with congestive heart failure or cardiomyopathies, may have left ventricular dysfunction, in which the normal electrical activation sequence through heart 6 is compromised within LV 28. Some patients may experience an intra-atrial conduction defect, such as intra-atrial block, in which the atrial activation is delayed because of conduction delays between LV 28 and RV 24. Some patients with LBBB and/or RBBB may experience an interventricular conduction defect in which electrical impulses are not conducted in a normal fashion along the respective right or left bundle branch. Ventricular asynchrony may result from conduction defects along the Bundle of His, the right or left bundle branches, and/or at the more distal Purkinje terminals. Typical intra-ventricular peak-to-peak asynchrony can range from about 80 milliseconds (ms) to about 200 ms or longer. However, in patients who are experiencing RBBB or LBBB, the QRS complex may be widened beyond the normal range, such as to about 120 ms to about 250 ms or greater.

CRT delivered by IMD 4 may help alleviate heart failure conditions (e.g., LV and/or RV dysfunction) by restoring synchronous depolarization and contraction of one or more chambers of heart 6. In some examples, fusion pacing or other CRT delivered to a heart (e.g., by IMD 4 to heart 6), as described herein, may increase stroke volume of heart 6 by improving the synchrony with which LV 28 and RV 24 depolarize and contract. Increasing a stroke volume of heart 6 may reduce symptoms of cardiac dysfunction experienced by the patient, may improve the patient's prognosis, or otherwise improve a clinical outcome for the patient. However, the duration of a cardiac cycle of heart 6 (e.g., a duration of a depolarization-repolarization sequence) may vary with changes in one or more physiological parameters of the patient, such as changes in heart rate. For example, as a heart rate of the patient changes, the timing of the delivery of a pacing pulse by IMD 4 to LV 28 during fusion pacing therapy or the timing of the delivery of pacing pulses by IMD 4 to LV 28 and RV 24 during biventricular pacing therapy may need to be changed to adapt CRT to the changing heart rate of the patient.

The techniques described herein advantageously may adapt CRT to meet changing needs of the patient by determining an updated a value of a CRT parameter according to which IMD 4 delivers the ventricular pacing, such as upon the expiration of a time period, when the processing circuitry determines that a physiological parameter (e.g., a heart rate and/or physical activity level) of the patient has changed, and/or when the processing circuitry otherwise determines that further adjustment of values of one or more CRT parameters may be desirable. Thus, techniques described herein may enable IMD 4 to maintain delivery of the ventricular pacing pulse at a time that results in a fusion of the depolarization of LV 28 and RV 24 despite changes in a physiological parameter of the patient and/or changes to system 2. In some examples in which the processing circuitry determines an updated value of a CRT parameter, such as an A-V delay for fusion pacing, at predetermined intervals, the processing circuitry may determine an updated value of the CRT parameter once per minute, once per hour, semi-continuously, or at another predetermined interval. In some examples, the processing circuitry may determine an updated value of a CRT parameter based on a detected change in heart rate that satisfies a threshold value, which may be indicative of the patient's sleep state or a physical activity level.

In any such examples, the processing circuitry may determine the updated value of the CRT parameter based on an identified target value of a metric of comparison associated with a relationship between a first activation interval between an occurrence of a first fiducial of a cardiac cycle and a second fiducial of the cardiac cycle detected in a first electrogram acquired by the processing circuitry during delivery of ventricular pacing by IMD 4 according to a sequence and a second activation interval between the occurrence of the first fiducial of the cardiac cycle and the second fiducial of the cardiac cycle detected in a second electrogram acquired by the processing circuitry during delivery of ventricular pacing by IMD 4 according to a sequence of different values of a CRT parameter, as described above. For example, the processing circuitry may acquire a first electrogram and a second electrogram from respective ones of a first vector formed from any bipolar combination of electrodes 30-49 and/or housing electrode 60 and a second electrode vector formed from any other bipolar combination of electrodes 30-49 and/or housing electrode 60.

The processing circuitry then may determine, for each of the different values of the CRT parameter of the sequence, a value of at least one metric of comparison of the first activation interval to the second activation interval. In some examples, the at least one metric of comparison may be at least one of a ratio between the first and second activation intervals (e.g., a ratio of the time duration of longer of the first and second activation intervals to the time duration of the shorter of the first and second activation intervals), a time difference between the first and second activation intervals, and/or one or more other suitable metrics. The processing circuitry then may control IMD 4 to deliver ventricular pacing at the updated value of the CRT parameter to provide CRT, such as until the processing circuitry determines that it is time to determine another updated value of the CRT parameter.

The configuration of medical device system 2 illustrated in FIG. 1 is one example configuration and is not intended to be limiting. As discussed in further detail below with respect to FIG. 4, housing 60 may enclose one or more accelerometers, therapy delivery circuitry, which may be configured to generate therapeutic stimulation, such as cardiac pacing, cardioversion, and defibrillation pulses, and sensing circuitry configured to sense electrical signals corresponding to a cardiac electrogram signal of the patient and/or an activity level or activity of the patient. Housing 60 also may enclose and one or more of a memory for storing default and/or allowable values of one or more therapy parameters (e.g., CRT parameters), diagnostics, feedback from the patient, and/or therapy programs that may include values of one or more CRT parameters. Housing 60 further may enclose communication circuitry configured for communication between IMD 4 and external device 8 and/or other devices, such as an external device located with a clinician or a server. Such components may enable IMD 4 to carry out one or more aspects of the techniques described herein, such as transmitting data pertaining to a physiological condition of the patient and/or one or more recommended values of one or more CRT parameters to external device 8.

In some examples, medical device system 2 may include one or more additional sensors, e.g., for sensing patient activity level, such as one or more accelerometers (not shown) or temperature sensors. The one or more accelerometers may comprise one or more three-axis accelerometers and may be a component of IMD 4 or a component of another IMD of system 2. Signals generated by such sensors may be indicative of, for example, gross body movement of the, such as a patient posture, exertion, temperature, or activity level. Regardless of the configuration of such sensors, processing circuitry of system 2 may determine values of one or more physiological parameters of the patient (e.g., patient posture and/or activity level) based on the signals obtained from such sensors, such as whether the patient's activity level is low, medium, high, associated with a numeric value, or associated with a particular activity or other value. In some such examples, the processing circuitry may determine an updated value of a CRT parameter based on the determination that values of the one or more physiological parameters of the patient have changed relative to a baseline value or other previously-determined value.

Although such processing circuitry may be contained within IMD 4 and/or within another IMD or other device of system 2, e.g., external device 8, the processing circuitry may be described herein as being a component of IMD 4 for the sake of clarity. The processing circuitry of IMD 4 then may use the determined patient parameter values pertaining to posture and/or activity level to determine a default value of a therapy parameter, such as a rate at which to deliver cardiac pacing to heart 6. As further described below, IMD 4 then may deliver CRT to heart 6 according to an updated value of a CRT parameter that the processing circuitry may determine based on the determined patient parameter value.

In some examples, IMD 4 also may provide defibrillation therapy and/or cardioversion therapy. For example, IMD 4 may detect arrhythmia of heart 6, such as fibrillation of the ventricles, and deliver defibrillation therapy to heart 6 in the form of electrical shocks. In some examples, IMD 4 may be programmed to deliver a progression of therapies, e.g., shocks with increasing energy levels, until a fibrillation of heart 6 is stopped. In examples in which IMD 4 provides defibrillation therapy and/or cardioversion therapy, IMD 4 may detect fibrillation by employing one or more suitable fibrillation detection techniques.

In other examples, medical device system 2 may include extravascular electrodes, such as subcutaneous electrodes, substernal electrodes, epicardial electrodes, and/or patch electrodes, instead of or in addition to the electrodes of leads 12, 14, and 16 illustrated in FIG. 1. In some other examples, a medical device configured to deliver cardiac therapy may not necessarily be implanted in the patient. In some such examples, a medical device may deliver defibrillation pulses, pacing pulses, and other therapies to heart 6 via percutaneous leads that extend through the skin of the patient to one or more locations within or outside of heart 6.

In some other examples, medical device system 2 may include any suitable number of leads coupled to IPG 56 and extending to any suitable location within or proximate to heart 6. For example, medical device system 2 may include a dual-chamber IMD instead of a three-chamber IMD such as IMD 4. In one example, a dual-chamber IMD may be electrically connected to a single lead that includes stimulation and sense electrodes within LV 28 as well as sense and/or stimulation electrodes within RA 22. In another example of a dual chamber configuration, IMD 4 is connected to two leads that extend into a respective one of RA 22 and LV 28.

Instead of or in addition to IMD 4, medical device system 2 may include one or more leadless (e.g., intracardiac) pacing devices (LPDs). In such examples, the one or more LPDs may include therapy delivery circuitry and processing circuitry within a housing configured for implantation in or within one of the chambers of heart 6. In such systems, the one or more pacing devices, which may include one or more LPDs and/or an IMD coupled to one or more leads, may communicate to coordinate sensing and pacing in various chambers of heart 6 to provide CRT according to the techniques described herein. Processing circuitry and memory of one or more of the pacing devices, and/or another implanted or external medical device, may provide the functionality for controlling delivery of CRT described with respect to processing circuitry of medical device system 2 and/or a memory of medical device system 2.

In some examples, one or more LPDs within or adjacent to RV 24 and/or LV 28 may act as slave devices to provide biventricular or fusion CRT. The master device that controls the timing of the delivery of pacing by the LPD(s) may be a leaded pacemaker or ICD (e.g., IMD 4), an extravascular ICD, or an implantable cardiac monitor, such as the REVEAL™ or LINQ™ insertable cardiac monitors commercially available from Medtronic, plc of Dublin, Ireland. The master device may include or be coupled to electrodes and may be configured to acquire one or more electrograms. The master device may be configured to determine values of CRT parameters for the delivery of ventricular pacing by the LPD(s) based on the electrograms acquired by the processing circuitry of medical device system 2 according to the techniques described herein.

External device 8 may be a computing device (e.g., used in a home, ambulatory, clinic, or hospital setting) to communicate with ICM 10 via wireless telemetry. External device 8 may include or be coupled to a remote patient monitoring system, such as Carelink®, available from Medtronic plc, of Dublin, Ireland. External device 8 may be, as an example, a programmer, external monitor, or a consumer device (e.g., a smart phone). In some examples, external device 8 may receive data, alerts, patient physiological information, or other information from IMD 4.

In some examples, external device 8 may be used to program commands or operating parameters into IMD 4 for controlling its functioning (e.g., when configured as a programmer for IMD 4). External device 8 may be used to interrogate IMD 4 to retrieve data, including device operational data as well as physiological data accumulated in IMD memory. The interrogation may be automatic, such as according to a schedule, or in response to a remote or local user command. Programmers, external monitors, and consumer devices are examples of external devices 18 that may be used to interrogate IMD 4. Examples of communication techniques used by IMD 4 and external device 8 include radiofrequency (RF) telemetry, which may be an RF link established via Bluetooth, WiFi, or medical implant communication service (MICS). In some examples, external device 8 includes processing circuitry. The processing circuitry of external device 8 may be configured to perform any of the techniques described with respect to processing circuitry of medical device system 2, such as described further herein.

FIG. 2 is a conceptual drawing illustrating portions of IMD 4 of FIG. 1 in conjunction with heart 6 and vectors that processing circuitry of medical device system 2 may use electrograms during an example technique to determine an updated value of a CRT parameter. FIG. 2 illustrates a portion of right ventricular lead 12 and left ventricular lead 16 positioned in heart 6. As illustrated in FIG. 2, example bipolar electrode vectors 70, 72, 74, and 76 may be formed from two or more electrodes selected from electrodes 30-49 and/or housing electrode 60 of IMD 4. In the example of FIG. 2, electrode vector 70 is formed between electrode 30 on lead 12 and housing electrode 60. Electrode vector 72 is formed between electrode 34 on lead 12 and a combination of electrodes 38 and 40 on lead 16. In electrode vector 72, electrodes 38 and 40 may be used in combination to form a single pole of electrode vector 72. Electrode vector 74 is formed between electrode 32 on lead 12 and electrode 42 on lead 16. Electrode vector 76 is formed between electrode 32 on lead 12 and electrode 48 on lead 16. It should be noted that electrode vectors 70-76 illustrated in FIG. 2 are example electrode vectors that may be used in the techniques described herein. In some examples, electrode vectors used in the techniques described herein may include other combinations of electrodes 30-49 and/or housing electrode 60 of IMD 4, such as combinations of electrodes 30-49 and/or housing electrode 60 of IMD 4 not being used to deliver pacing pulses during a technique to determine an updated value of a CRT parameter.

Additionally, or alternatively, an electrode on any of leads 12, 14, or 16 may be used in combination with one or more of the other electrodes on the same one of leads 12, 14, or 16 to form a single pole of an electrode vector, in a manner similar to electrodes 38 and 40 of electrode vector 74.

In some techniques for determining an updated value of a CRT parameter, the processing circuitry may control IMD 4 to deliver ventricular pacing to heart 6 at a sequence of different values of the CRT parameter. For example, the processing circuitry may control IMD 4 to deliver LV fusion pacing, such as via electrodes 44 and 46 on lead 16, although the processing circuitry may control IMD 4 to deliver ventricular pacing according to different CRT modes and/or electrode configurations in other examples. The processing circuitry may acquire, during delivery of ventricular pacing by IMD 4 according to the sequence, a first electrogram and a second electrogram, which may be unipolar or bipolar, from respective ones of a first electrode vector formed from electrodes 30-49 and/or housing electrode 60 and a second electrode vector formed from electrodes 30-49 and/or housing electrode 60. In some examples, the first and second electrode vectors may be two electrode vectors of electrode vectors 70, 72, 74, and 76 illustrated in FIG. 2 and/or other electrode vectors formed from electrodes 30-49 and/or housing electrode 60. For example, electrode vector 72 may be a first electrode vector and electrode vector 76 may be a second electrode vector. In some examples, the first and second electrode vectors may share an electrode (i.e., include a common electrode), such as examples in which electrode vectors 70 and 72 are first and second electrode vectors, or examples in which electrode vectors 74 and 76 are first and second electrode vectors. In other examples, the first and second electrode vectors may not share any electrodes in common.

The processing circuitry may acquire the first electrogram by subtracting a signal of at least one first electrode of the first vector from at least one second electrode of the first electrode vector and acquire the second electrogram by subtracting a signal of at least one first electrode of the second electrode vector from at least one second electrode of the second electrode vector. For example, in an example technique in which electrode vector 72 is a first electrode vector and electrode vector 76 is a second electrode vector, the processing circuitry may acquire a first electrogram by subtracting a signal from electrode 34 on lead 12 from a combined signal from electrodes 38 and 40 on lead 16. The processing circuitry may acquire a second electrogram by subtracting a signal from electrode 32 on lead 12 from a signal from electrode 48 on lead 16.

The processing circuitry then may determine, for each of the different values of the CRT parameter, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram and at least one metric of comparison of the first activation interval to the second activation interval, such as at least one of a ratio between the first and second activation intervals (e.g., a ratio of the time duration of longer of the first and second activation intervals to the time duration of the shorter of the first and second activation intervals) and/or a time difference between the first and second activation intervals. The processing circuitry then may identify a target value of the at least one metric of comparison and determine an updated value of a CRT parameter based on the target value.

In any such examples, the first and second electrode vectors may be substantially orthogonal to one another, such as electrode vectors 72 and 76. In some examples, the first and second electrode vectors may be considered to be substantially orthogonal to one another when the first and second electrode vectors are positioned as close to about 90 degrees relative to one another as possible based on the placement of the available electrodes. In some examples, the first and second electrode vectors may be positioned about 90 degrees relative to each other. However, in other examples, such as examples in which no electrode vectors positioned about 90 degrees relative to each other are available, the first and second electrode vectors may be considered substantially orthogonal if they are positioned about 45 degrees to about 90 degrees relative to one another. In some examples of the techniques described herein, the use of orthogonal first and second electrode vectors may help enable determination of a value of at least one metric of comparison of a first activation interval to a second activation interval that the processing circuitry may determine in associated with a value of a CRT parameter. For example, first and second electrograms that the processing circuitry may acquire from respective orthogonal first and second electrode vectors may better illustrate a difference between the first and second activation intervals because such first and second electrograms may better depict a cardiac cycle from two different perspectives than first and second electrograms acquired from respective first and second electrode vectors that are more similarly oriented.

First and second electrograms that depict the cardiac cycle from two different perspectives (e.g., first and second electrograms acquired from orthogonal first and second electrode vectors) may better illustrate differences in a rate of conduction of electrical impulses through heart 6 that may result from delivery of CRT according to different values of a CRT parameter. As further discussed below with respect to FIGS. 3A and 3B, differences in values of at least one metric of comparison of the first activation interval to the second activation interval associated with delivery of ventricular pacing at different values of the CRT parameter may correspond to differences in the rate of conduction of electrical impulses through the heart (e.g., the ventricles) resulting from delivery of ventricular pacing by IMD 4 to heart 6 at the different values. The target value may be associated with a value of the CRT parameter at which the value of the ratio of the longer of the first and second activation intervals to the shorter of the first and second activation intervals is within a threshold distance of a value of 1 and/or a value at which a time difference between the first activation interval and the second activation interval is at a minimum or at or below a threshold, which may be a value of the CRT parameter resulting in an improved (e.g., increased) rate of conduction of electrical impulses through heart 6 in examples in which the patient has a conduction dysfunction. Thus, example techniques in which the first and second electrode vectors are orthogonal to one another may provide an indication of a degree of ventricular synchrony that allows processing circuitry determine an updated value of a CRT parameter that may be associated with an improvement in a conduction dysfunction of heart 6. Delivery of ventricular pacing by IMD 4 at a value of a CRT parameter associated with an improvement in a conduction dysfunction of heart 6 may result in an efficacious outcome of CRT for the patient (e.g., improvement of symptoms and/or other markers of efficacious CRT).

In some examples, the first fiducial may correspond to a time at which IMD 4 delivers a pacing pulse to heart 6. In other examples, the first fiducial may be a feature of a cardiac cycle occurring prior to the occurrence of the second fiducial. The second fiducial may correspond to a feature of the first and second electrograms related to depolarization of the heart in response to the pacing pulse, such as one of an onset of a paced ventricular activation in the first and second electrograms (e.g., onset of activation of LV 28 in examples in which IMD 4 delivers LV fusion pacing), a maximum dv/dt, a detected R-wave in the first and second electrograms, or a maximum amplitude of the first electrogram and the second electrogram. In some examples in which the second fiducial is an R-wave, the processing circuitry may detect the occurrence of the second fiducial in an electrogram by comparing the amplitude of the electrogram to a threshold and detecting the occurrence of the R-wave when the amplitude of the electrogram satisfies the threshold amplitude. In other such examples, the processing circuitry may detect the occurrence of the R-wave based on the timing of the maximum amplitude of the electrogram or an occurrence of an amplitude associated with R-wave onset.

In some such examples, the processing circuitry may determine the time of the occurrence of the first fiducial of the cardia cycle as being a time at which therapy delivery circuitry of IMD 4 delivers a pacing pulse during the cardiac cycle. In other examples, such as examples in which the first fiducial does not correspond to the time of delivery of a pacing pulse by IMD 4, the processing circuitry may determine the time of the occurrence of the first fiducial by detecting the first fiducial (e.g., a feature of the cardiac cycle occurring prior to the second fiducial) in the first and second electrograms.

According to the techniques described herein, the processing circuitry may determine an updated value of a CRT parameter by determining an updated A-V and/or V-V delay by based on the target value. In some examples, the processing circuitry may determine an updated A-V delay and an updated V-V delay by either determining two A-V delays (e.g. an A-RV delay and an A-LV delay) or by determining one A-V delay and one V-V delay. Thus, techniques for adjusting A-V and V-V delays described herein should be understood to include either approach.

The techniques described herein may be performed with IMD 4 operating in either a biventricular-pacing CRT mode or fusion-pacing CRT mode. For example, during delivery of left-ventricular fusion pacing by IMD 4, processing circuitry of medical device system 2 (e.g., processing circuitry of IMD 4) may determine the RA to RV conduction time, rather than control it by means of an RA-RV pacing interval as would be the case for biventricular pacing.

Figure 3A:
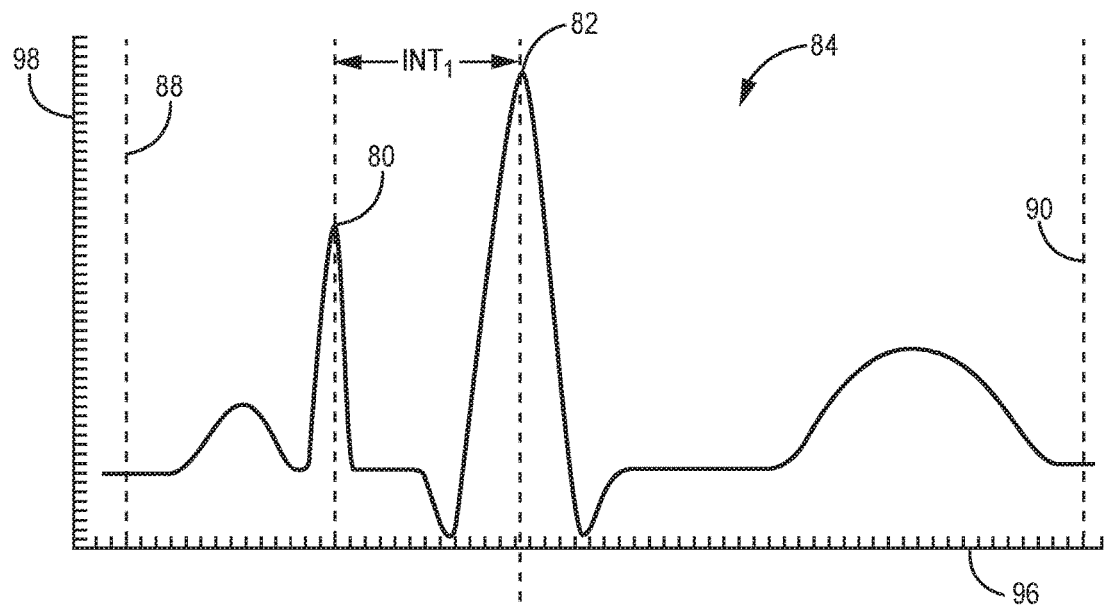
FIGS. 3A and 3B are conceptual drawings illustrating a first activation interval between an occurrence of a first fiducial of a cardiac cycle and a second fiducial of the cardiac cycle depicted in a first electrogram, a second activation interval between an occurrence of the first fiducial of the cardiac cycle and the second fiducial of the cardiac cycle depicted in a second electrogram, and a difference in time between the occurrence of the second fiducial in the first electrogram and the occurrence of the second fiducial in the second electrogram.
Figure 3B:
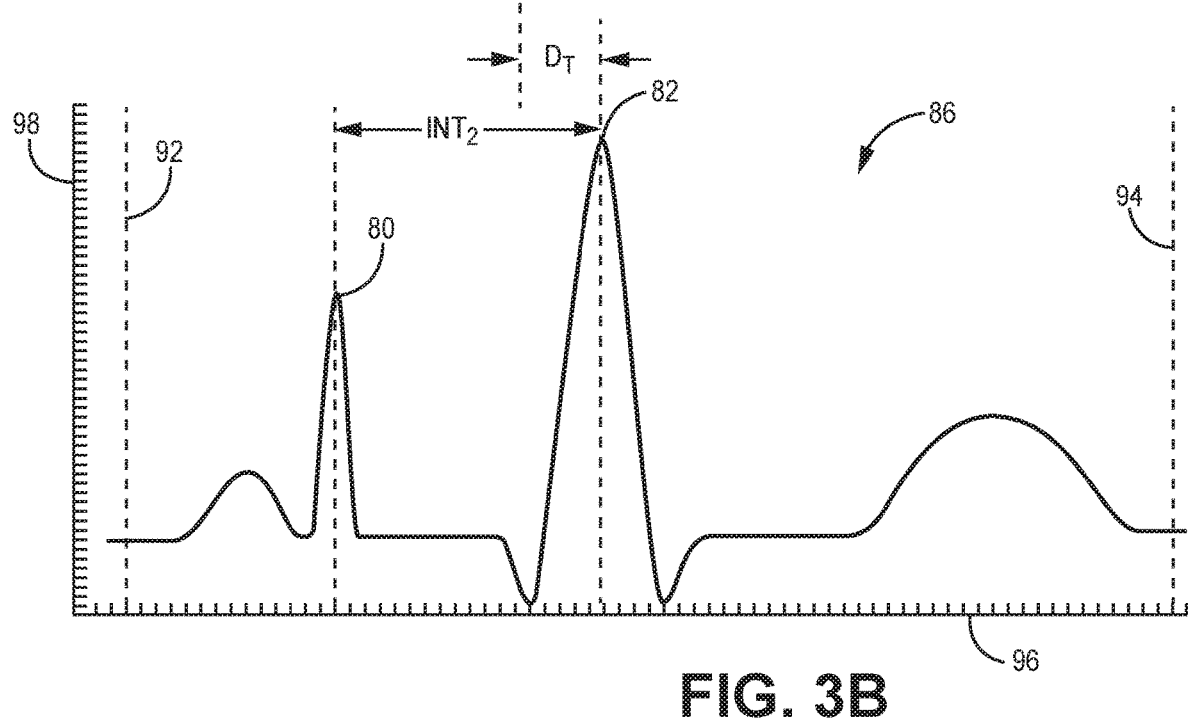

FIGS. 3A and 3B are conceptual drawings illustrating a first activation interval $INT_1$ between an occurrence of a first fiducial 80 of a cardiac cycle and a second fiducial 82 of the cardiac cycle detected in a first electrogram 84, a second activation interval $INT_2$ between an occurrence of the first fiducial 80 of the cardiac cycle and the second fiducial 82 of the cardiac cycle detected in a second electrogram 86, and a difference in time $D_T$ between the occurrence of the second fiducial in the first electrogram 84 and the occurrence of the second fiducial in the second electrogram 86. The cardiac cycle detected in first electrogram 84 is illustrated in FIG. 3A as extending between point 88 and point 90 of first electrogram 84 and the cardiac cycle detected in second electrogram 86 is illustrated in FIG. 3B as extending between point 92 and point 94 of second electrogram 86. The illustrations of first electrogram 84 of FIG. 3A and second electrogram 86 of FIG. 3B include the time component 96 of first and second electrograms 84, 86 along the X-axes thereof and the amplitude component 98 along the Y-axes thereof. Processing circuitry (e.g., processing circuitry of IMD 4) may acquire first electrogram 84 and second electrogram 86 from respective first and second electrode vectors formed from electrodes 30-49 and 60 of medical device system 2. For example, the processing circuitry may acquire first electrogram 84 and second electrogram 86 from respective ones of electrode vector 72 and electrode vector 76 illustrated in FIG. 2.

Processing circuitry may acquire first electrogram 84 and second electrogram 86 during delivery of ventricular pacing by IMD 4 according to a value of a CRT parameter. In the example of FIGS. 3A and 3B, first fiducial 80 is a pacing spike in the amplitude of electrograms 84, 86 corresponding to delivery of a pacing pulse (e.g., to LV 28) by IMD 4 during the cardiac cycle according to the CRT parameter. First fiducial 80 may be a pacing spike in examples in which one medical device (e.g., an implantable cardiac monitor or an external medical device) is used to sense cardiac electrical signals according to the techniques described herein and another medical device (e.g., IMD 4) is used to deliver ventricular pacing. In such examples, processing circuitry of the medical device that senses cardiac electrical signals may detect and distinguish the pacing spike from intrinsic cardiac electrical activity based on one or more criteria (e.g., amplitude and/or slew rate), each of which may be expected to be greater than that of intrinsic cardiac signals.

It should be noted that the illustrations of first fiducial 80 in FIGS. 3A and 3B are intended to show that first fiducial 80 generally precedes second fiducial 82 in a cardiac cycle. Thus, one or more aspects of the first fiducial 80 illustrated in FIGS. 3A and 3B (e.g., width, amplitude, and/or proportion relative to other features of the cardiac cycles detected in electrograms 84, 86) may not necessarily be shown to scale of a particular pacing spike that may be observed in an electrogram. In other examples, such as examples in which IMD 4 both senses cardiac electrical signals and delivers ventricular pacing, the processing circuitry may otherwise determine the timing of the pacing pulse, e.g., based on the time at which the processing circuitry controlled IMD 4 to deliver the pacing pulse.

Second fiducial 82 is a maximum amplitude of a detected R-wave in electrograms 84, 86, which in this example also is a maximum amplitude of the electrograms 84, 86. $INT_1$ and $INT_2$ represent time intervals between occurrences of first fiducial 80 and second fiducial 82 in first electrogram 84 and second electrogram 86, respectively. Because the electrode vectors from which the processing circuitry may acquire first electrogram 84 and second electrogram 86 extend in different planes relative to heart 6 (e.g., orthogonally), first electrogram 84 and second electrogram 86 represent the cardiac cycle from different perspectives relative to heart 6. The difference in perspectives from which electrograms 84, 86 detect the cardiac cycle is illustrated by the difference in time $D_T$ between the occurrence of the second fiducial in the first electrogram 84 and the occurrence of the second fiducial in the second electrogram 86. In some examples, the difference in time $D_T$ may be a metric of comparison of the first activation interval to the second activation interval that the processing circuitry may determine as a value of a metric of comparison of the first activation interval to the second activation interval.

The magnitude of $D_T$ may be associated with a rate of conduction of electrical impulses through heart 6. For example, a larger value of $D_T$ may be associated with a lower rate of conduction of an electrical impulse through heart 6 and a smaller value of $D_T$ may be associated with a higher rate of conduction of an electrical impulse through heart 6. Thus, an occurrence of conduction dysfunction (e.g., conduction delay) of heart 6 may be associated with a relatively larger value of $D_T$. In such examples, delivery of efficacious CRT to heart 6, which may reduce conduction dysfunction by increasing conduction rate, may be associated with a relatively smaller value of $D_T$. In some such examples, a target value of $D_T$ associated with increased conduction rate may be a value of $D_T$ that is equal to or less than a threshold value, or a value of $D_T$ that is a minimum value relative to other values of $D_T$ resulting from delivery of CRT according to other values of a CRT parameter. In some examples, such an increased conduction rate may correspond to fusion occurring between left ventricular activation and right ventricular activation, which may provide hemodynamic benefit to the patient.

During a technique to determine an updated value of a CRT parameter, as illustrated in the example of FIGS. 3A and 3B, the processing circuitry may control IMD 4 to deliver ventricular pacing according to a sequence of different values of the CRT parameter and acquire first electrogram 84 and second electrogram 86 during delivery of ventricular pacing by IMD 4. The processing circuitry may determine $INT_1$, occurring between first fiducial 80 and second fiducial 82 in first electrogram 84 and determine $INT_2$, occurring between first fiducial 80 and second fiducial 82 in second electrogram 86 for each of the different values of the CRT parameter.

As discussed above, in some examples, the processing circuitry may determine $INT_1$ and $INT_2$ by detecting both first fiducial 80 of and the second fiducial 82 in respective ones of first electrogram 84 and second electrogram 86. However, in other examples, the processing circuitry determine a time of an occurrence of first fiducial 80 based on a time at which IMD 4 delivers a pacing pulse to heart 6 instead of detecting first fiducial 80 in first electrogram 84 and second electrogram 86. For example, the time at which IMD 4 delivers the pacing pulse may be "known" to timing and/or control aspects of the processing circuitry. Thus, the determination of a time of an occurrence of first fiducial 80 is not necessarily dependent upon signal detection from an electrode vector and analysis of first electrogram 84 and/or second electrogram 86, which in some examples may simplify and/or enhance the accuracy of the determination of $INT_1$ and $INT_2$ by the processing circuitry.

Processing circuitry then may determine a value of $D_T$ for each value of the different values sequence according to which IMD 4 delivers ventricular pacing. For example, the processing circuitry may determine a value of $D_T$ by subtracting $INT_1$ from $INT_2$. The processing circuitry then may identify the target value of $D_T$, such as by determining a minimum value of $D_T$ (e.g., a minimum value of $D_T$ among the determined values of $D_T$) or a value of $D_T$ that is equal to or less than a threshold value of $D_T$.

In other examples, in addition to or instead of determining target value of $D_T$, the processing circuitry may determine a target value of at least one other metric of comparison of the first activation interval to the second activation interval, such as a ratio of the larger of $INT_1$ and $INT_2$ to the smaller of $INT_1$ and $INT_2$ for each value of the CRT parameter of the sequence and determine a target value of the ratio. Values a CRT parameter associated with a ratio of $INT_1$ to $INT_2$ that is closer to 1:1 (i.e., a value of 1) than other values of the CRT parameter may be associated with increased conduction rate in heart 6. Thus, the processing circuitry may identify a target value of the ratio of $INT_1$ to $INT_2$ by determining a value of with the ratio of $INT_1$ to $INT_2$ that is closest to a value of 1 or within a threshold distance from a value of 1, or by determining a value of $D_T$ that is a minimum value relative to other values of the ratio of $INT_1$ to $INT_2$ resulting from delivery of CRT according to other values of a CRT parameter.

In any such examples, the processing circuitry may determine the updated value of the CRT parameter based on the identified target value of $D_T$ and/or the identified target value of the ratio of $INT_1$ to $INT_2$. For example, the processing circuitry may determine the updated value of the CRT parameter as being the value of the CRT parameter that resulted in the target value of $D_T$ and/or or the target value of the ratio of $INT_1$ to $INT_2$. The processing circuitry then may control IMD 4 to deliver ventricular pacing at the updated value of the CRT parameter to deliver CRT. For example, in examples in which the CRT parameter is A-LV delay, the processing circuitry may control IMD 4 to deliver LV fusion pacing at the value of A-LV delay that resulted in the target value of $D_T$ and/or or the target value of the ratio of $INT_1$ to $INT_2$.

Figure 4:
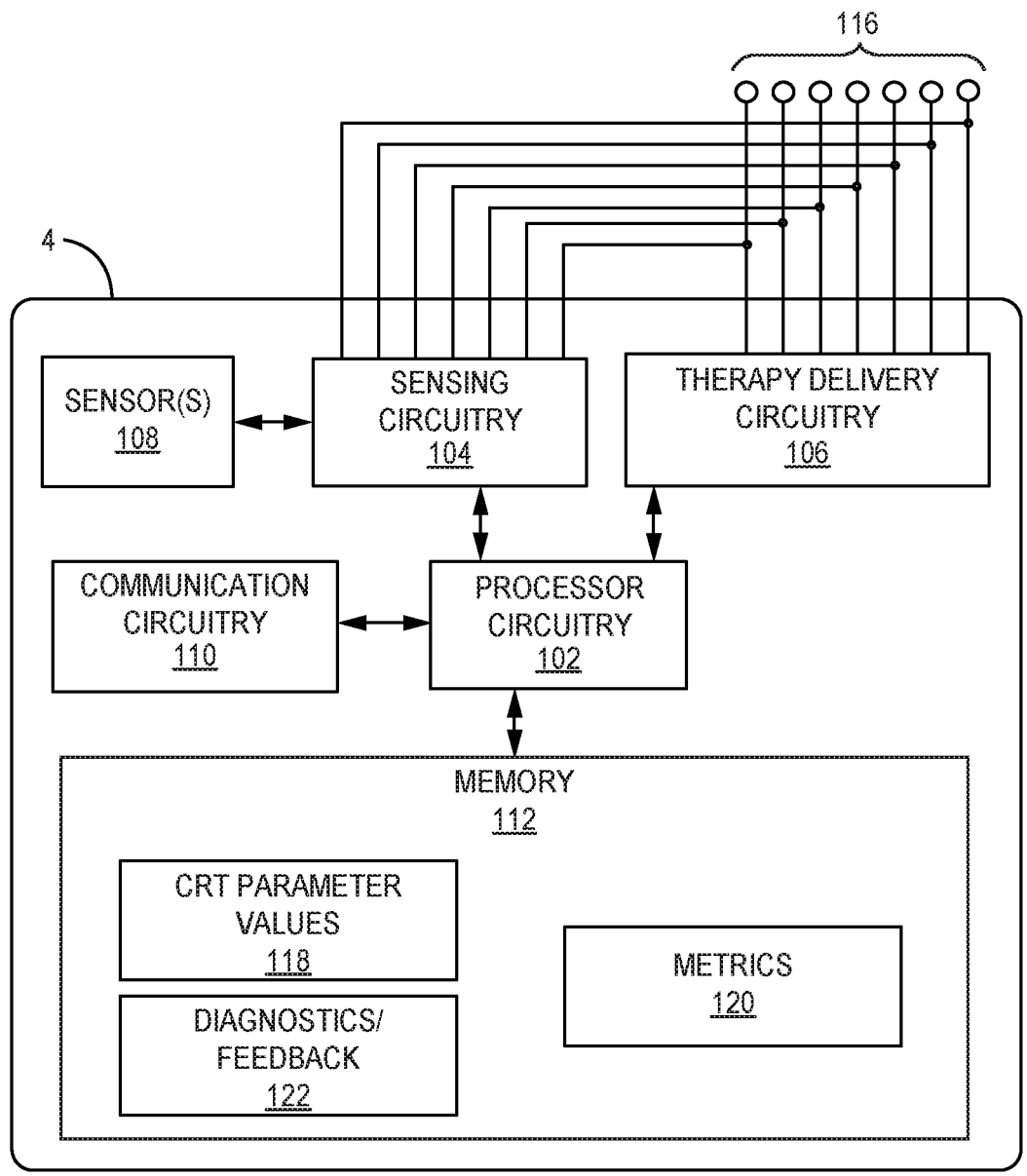
FIG. 4 is a functional block diagram illustrating an example configuration of an example implantable medical device.

FIG. 4 is a functional block diagram illustrating an example configuration of IMD 4. As shown in FIG. 4, IMD 4 includes processing circuitry 102, sensing circuitry 104, therapy delivery circuitry 106, sensors 108, communication circuitry 110, and memory 112. In addition, IMD 4 includes one or more electrodes 116, which may be any one or more of the previously-described electrodes of IMD 4, and one or more of which may be disposed on or within housing of IMD 4 or carried one or more of leads 12, 14, and/or 16 connected to IMD 4. In some examples, memory 112 includes computer-readable instructions that, when executed by processing circuitry 102, cause IMD 4 and processing circuitry 102 to perform various functions attributed to IMD 4 and processing circuitry 102 herein. Memory 112 may include any volatile, non-volatile, magnetic, optical, or electrical media, such as a random-access memory (RAM), read-only memory (ROM), non-volatile RAM (NVRAM), electrically erasable programmable ROM (EEPROM), flash memory, or any other digital media.

Processing circuitry 102 may include fixed function circuitry and/or programmable processing circuitry. Processing circuitry 102 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 102 may include multiple components, such as any combination of one or more microprocessors, one or more controllers, one or more DSPs, one or more ASICs, or one or more FPGAs, as well as other discrete or integrated logic circuitry. The functions attributed to processing circuitry 102 herein may be embodied as software, firmware, hardware or any combination thereof.

In some examples, processing circuitry 102 may monitor the passage of time to determine when a period has elapsed, such as a period during which IMD 4 may deliver cardiac pacing according an initial value of a CRT parameter, a patient-specific value of the CRT parameter previously determined by processing circuitry 102, or a value of the CRT parameter requested by a user. As illustrated in FIG. 4, memory 112 may include one or more of CRT parameter values 118, metrics 120, and/or diagnostics/feedback data 122. In some examples, CRT parameter values 118 may include an updated value of a CRT parameter at which processing circuitry 102 may control IMD 4 to deliver ventricular pacing. CRT parameter values may include a plurality of other different values of the CRT parameter, such as a sequence of different values of the CRT parameter at which processing circuitry 102 may control IMD 4 to deliver ventricular pacing during a technique to determine a patient-specific updated value of a CRT parameter. CRT parameter values may be one or more values of one or more corresponding CRT parameters, such as one or more values of an A-V delay or a V-V delay.

Metrics 120 may include values associated with relationships between first and second activation intervals corresponding to one or more values of one or more CRT parameters. For example, metrics 120 may include values of first and second activation intervals that processing circuitry 102 may determine for different values of one or more CRT parameters, values of ratios of first activation interval to a second activation interval associated with different values of one or more CRT parameters, and/or values of time differences between a first activation interval and a second activation interval (e.g., $D_T$ values) associated with different values of one or more CRT parameters As described above, processing circuitry 102 of IMD 4 in some examples may be configured to determine an updated value of the CRT parameter upon determining that a time period has elapsed, that a physiological parameter of the patient has changed, and/or otherwise determining that adjustment of the value of the CRT parameter may be desirable. Processing circuitry 102 may determine the updated value of the CRT parameter according to the example techniques described herein and store the updated value in CRT parameter values 118. For example, processing circuitry 102 may control IMD 4 to deliver CRT according to a sequence of different values of CRT parameter values 118, acquire a first electrogram and a second electrogram, determine a first activation interval, a second activation interval, and a value of a a metric of comparison for each of CRT parameter values 118 of the sequence, identify a target value of the a metric of comparison, and determine the updated value of the CRT parameter based on the target value.

In some examples, processing circuitry 102 may store the determined target values in metrics 120. For example, processing circuitry 102 may store, in association with one or more of CRT parameter values 118, at least one corresponding value of a metric of comparison of the first activation interval to the second activation interval determined by processing circuitry 102. In some examples, processing circuitry 102 also may be configured to determine one or more values of one or more corresponding physiological parameters of the patient during delivery of CRT by IMD 4 according to a value of a CRT parameter, and store the one or more values of the corresponding physiological parameters in metrics 120 in association with at least corresponding value of a metric of comparison determined by processing circuitry 102 during delivery by IMD 4 of CRT according to a value of a CRT parameter.

In some such examples, processing circuitry 102 may determine an updated value of a CRT parameter, such as based on an expiration of a time period, based on one or more of metrics 120 stored in memory 112 in association with one or more values of one or more corresponding physiological parameters of the patient during delivery of CRT by IMD 4 according to a value of a CRT parameter. For example, if a relatively short period of time has passed between one or more previous determinations of an updated value of a CRT parameter by processing circuitry 102 and a determination by processing circuitry 102 to again update the value of the CRT parameter, a relationship between the one or more values of the physiological parameters of the patient, one or more of activation interval ratios or time differences 120, and a particular value of the CRT parameter may remain substantially unchanged. In such examples, it may not be necessary to re-determine at least one ratio of, and/or time difference between, first and second activation intervals for the particular value of the CRT parameter at that time. Thus, in some such examples, processing circuitry 102 may select an updated value of a CRT parameter from CRT parameter values 118 based on one or more determined current values of one or more corresponding physiological parameters of the patient without controlling IMD 4 to deliver CRT pacing according to a sequence of different values of a CRT parameter, which may improve an efficiency of operation of medical device system 2. In some such examples, processing circuitry 102 may determine new relationships between values of one or more physiological parameters of the patient, one or more of activation interval ratios or time differences 120, and a value of CRT parameters 118 and store such new relationships in memory 112, such as periodically or based on a request received from a remote computer.

In some examples, processing circuitry 102 may transmit data to a remote computer, such as data pertaining to changes in patient physiological parameters and/or one or more updated values of one or more corresponding CRT parameters 118 determined by processing circuitry 102 according to the techniques described herein. For example, processing circuitry 102 may transmit data pertaining to one or more aspects of patient cardiac function determined by processing circuitry 102 at different levels of patient physical activity, which may help the clinician determine whether changes in the patient's disease state have occurred and/or whether CRT delivered by IMD 4 remains an appropriate therapy for the patient.

Sensing circuitry 104 and therapy delivery circuitry 106 may be selectively coupled to electrodes 116, e.g., via switching circuitry (not shown) as controlled by processing circuitry 102. The switching circuitry may include one or more transistors or other circuitry for selectively coupling electrodes 116 to circuitry of IMD 4. Sensing circuitry 104 may monitor signals from electrodes 116 in order to monitor electrical activity of heart (e.g., to detect depolarizations for heart rate determination and/or to produce electrograms for determining updated values of a CRT parameter). Sensing circuity 104 may also monitor signals from one or more other sensor(s) 108, such as to determine an activity level or activity of the patient. In some examples, sensors 108 may be one or more accelerometers e.g., one or more three-axis accelerometers), one or more temperature sensors, or one or more other sensors configured to sense physical parameters of the patient. Signals generated by such sensors may be indicative of physical parameters of the patient, such as gross body movement, posture, exertion, temperature, activity level, or other physical parameters. Sensing circuitry 104 may monitor signals from electrodes 116 and sensors 108. In some examples, sensing circuitry 104 may include one or more filters and amplifiers for filtering and amplifying signals received from one or more of electrodes 116 and/or the one or more of sensor(s) 108. Sensing circuitry 104 may also include rectification circuitry, sample-and-hold circuitry, one or more comparators, and/or analog-to-digital conversion circuitry. The functionality provided by such circuitry may be applied to the signal in the analog or digital domain.

Based on the signals or indications or values determined from the signals received from sensing circuitry 104, processing circuitry 102 may determine current values of one or more physiological parameters of the patient. For example, processing circuitry may determine one or more of a of a heart rate, waking/sleeping state, or activity level of the patient, such as in response to determining that a time period has elapsed. In some examples, processing circuitry 102 may determine the activity level or activity of the patient based on signals received from sensing circuitry 104 that may be indicative of one or more physiological parameters, such as signals indicative of movement received from one or more accelerometers. In some examples, processing circuitry 102 additionally may determine the activity level or activity of the patient based on a thoracic impedance signal received from sensing circuitry 104, which may be indicative of respiration, e.g., a magnitude or depth and/or rate indicative of respiration of the patient.

In some examples, processing circuitry 102 may determine whether to determine an updated value of CRT parameter based on the current values of the one or more physiological parameters of the patient. For example, processing circuitry 102 may compare a current value of a physiological parameter of the patient to a previously-determined value or baseline value of the physiological parameter. If a difference between the current value of the physiological parameter and the previously determined value or baseline value of the physiological parameter satisfies a threshold difference, processing circuitry 102 may determine an updated value of the CRT parameter according to the techniques described herein and control IMD 4 to deliver CRT to heart 6 at the updated value of the CRT parameter. In this manner, processing circuitry enable medical device system 2 to adapt one or more values of a CRT parameter at which IMD 4 delivers CRT to changes in physiological parameters of the patient.

Therapy delivery circuitry 106 may include circuitry for generating a signal, such as one or more capacitors, charge pumps, and/or current sources, as well as circuitry for selectively coupling the signal to electrodes 116, e.g., transistors or other switching circuitry. In some examples, therapy delivery circuitry 106 may include a timer for determining that a period of time corresponding to an A-V or V-V delay at which IMD 4 is delivering CRT has elapsed since the delivery of the immediately preceding pacing pulse or intrinsic depolarization. Processing circuitry 102 may control therapy delivery circuitry 106 to deliver a pacing pulse at the value of the CRT parameter upon determining that such a period of time has elapsed. For example, processing circuitry 102 may generate a trigger signal that triggers the output of a pacing pulse by therapy delivery circuitry 106.

Communication circuitry 110 may include any suitable hardware, firmware, software or any combination thereof for communicating with another device, such as external device 8, or another IMD or sensor. For example, communication circuitry 110 may include voltage regulators, current generators, oscillators, or circuitry for generating a signal, resistors, capacitors, inductors, and other filtering circuitry for processing received signal, as well as circuitry for modulating and/or demodulating a signal according to a communication protocol. Communication circuitry 110 may also include transistors or other switching circuitry for selectively coupling transmitted signal to or receiving signals from an antenna of IMD 4 (not shown) or electrodes 116. Under the control of processing circuitry 102, communication circuitry 110 may receive downlink telemetry from, as well as send uplink telemetry to, external device 8 or another device. In some examples, communication circuitry 110 may communicate with external device 8. In addition, communication circuitry 110 may communicate with a networked computing device via an external device (e.g., external device 8) and a computer network, such as the Medtronic CareLink® Network developed by Medtronic, plc, of Dublin, Ireland, as further described below with respect to FIG. 5.

The patient, a clinician, or another user may retrieve data from IMD 4 using external device 8, or by using another local or networked computing device (e.g., a remote computer located with the clinician) configured to communicate with processing circuitry 102 via communication circuitry 110. In some examples, the clinician may also program parameters of IMD 4 using external device 8 or another local or networked computing device. Diagnostics/feedback 122 of memory 112 may store data pertaining to patient physiological parameters and/or the efficacy of CRT delivered by IMD 4. For example, diagnostics/feedback 122 may store efficacy determinations associated with delivery of CRT by IMD 4 at one or more values of one or more corresponding CRT parameters.

In some such examples, diagnostics/feedback 122 may store efficacy determinations based on an indication of efficacy of CRT entered by the patient into external device 8 and received by IMD 4. Diagnostics/feedback 122 also may store efficacy determinations made by processing circuitry 102 based on data pertaining to symptoms or undesired effects experienced by the patient before, during, and/or after delivery of CRT by IMD 4. In some examples, diagnostics/feedback 122 may store system diagnostics pertaining to the functioning of IMD 4 or other components of a medical device system including IMD 4. In any such examples, communication circuitry may communicate data pertaining to patient physiological parameters and/or the efficacy of CRT to a remote computer, such as a remote computer located with a clinician.

Although processing circuitry 102 of IMD 4 is described above as being configured control IMD 4 to deliver ventricular pacing according to a sequence of different values of a CRT parameter, acquire first and second electrograms from respective first and second electrode vectors formed from a plurality of electrodes of medical device system 2, determine an updated value of a CRT parameter, control IMD 4 to deliver ventricular pacing at the updated value of the CRT parameter, and carry out other steps of the techniques described herein, any steps described herein as being carried out by processing circuitry 102 of IMD 4 may carried out by processing circuitry of one or more other devices. For example, processing circuitry of external device 8, a remote computer, or any other suitable implantable or external device or server, may be configured to carry out one or more of the steps of the techniques described herein, such as via communication circuitry of 110 IMD 4.

Figure 5:
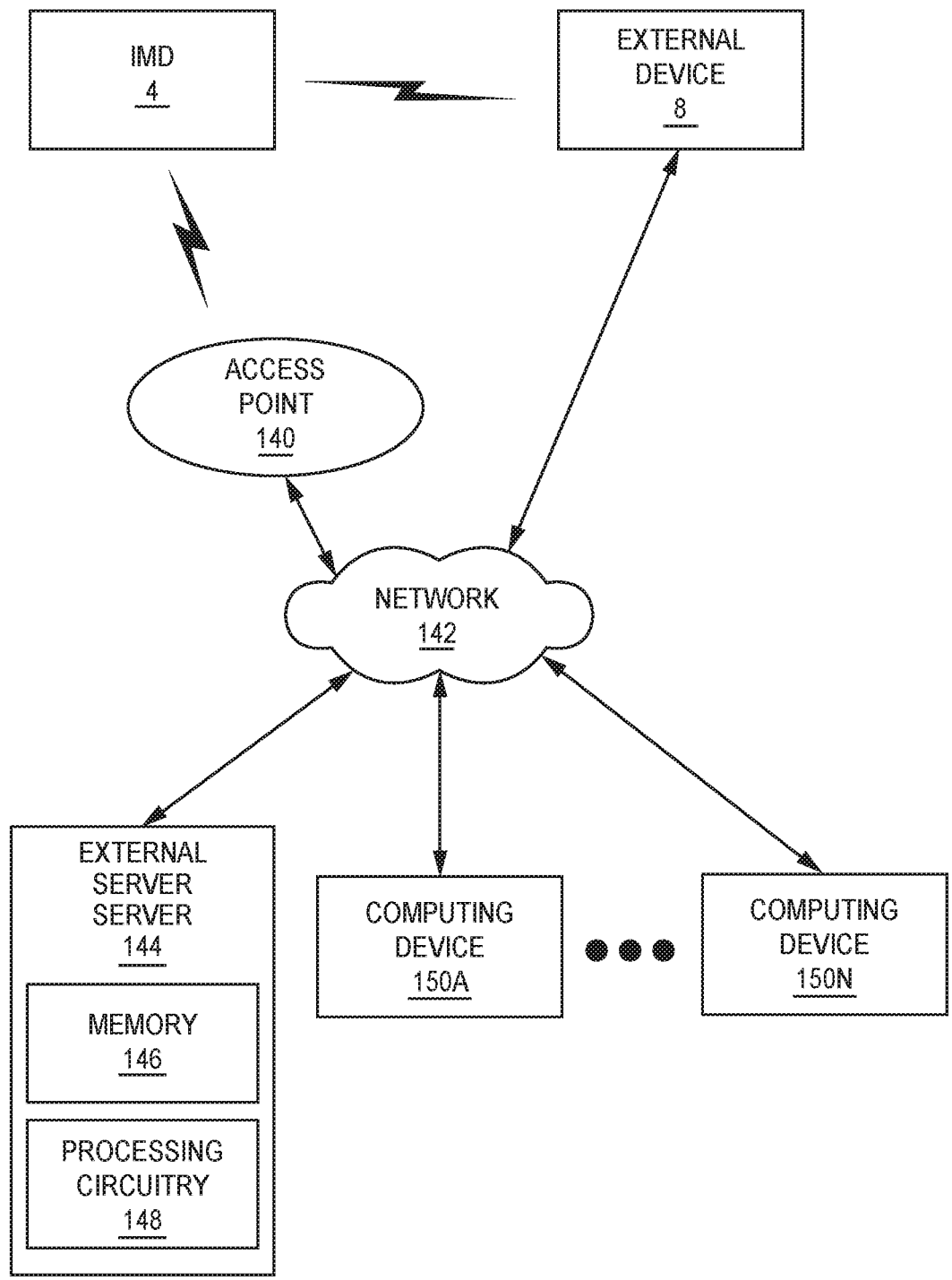
FIG. 5 is a functional block diagram illustrating an example system that includes an external device, such as a server, and one or more computing devices that are coupled to the implantable medical device and the external device of FIG. 1 via a network.

FIG. 5 is a functional block diagram illustrating an example system that includes an access point 140, a network 142, external computing devices, such as a server 144, which may include a memory 146 and/or processing circuitry 148, and one or more other computing devices 150A-150N, which may be coupled to IMD 4 and external device 8 via network 142. In this example, IMD 4 may use communication circuitry 110 to communicate with external device 8 via a first wireless connection, and to communicate with an access point 140 via a second wireless connection. In the example of FIG. 5, access point 140, external device 8, server 144, and computing devices 150A-150N are interconnected and may communicate with each other through network 142.

Access point 140 may comprise a device that connects to network 142 via any of a variety of connections, such as telephone dial-up, digital subscriber line (DSL), or cable modem, or other suitable connections. In other examples, access point 140 may be coupled to network 142 through different forms of connections, including wired or wireless connections. In some examples, access point 140 may be a user device, such as a tablet or smartphone, that may be co-located with the patient. As discussed above, IMD 4 may be configured to transmit data, such as current values and heart failure statuses, to external device 8. In addition, access point 140 may interrogate IMD 4, such as periodically or in response to a command from the patient, a clinician, or network 142, in order to retrieve data pertaining to one or more of patient symptoms, undesired effects, efficacy indications, CRT parameter values 118, metrics 120, diagnostics/feedback 122, or other information stored in memory 112 of IMD 4. Access point 140 may then communicate the retrieved data to server 144 via network 142.

In some cases, memory 146 of server 144 may be configured to provide a secure storage site for data collected from IMD 4 and/or external device 8. In some cases, server 144 may assemble data in web pages or other documents for viewing by trained professionals, such as clinicians, via computing devices 150A-150N. One or more aspects of the illustrated system of FIG. 5 may be implemented with general network technology and functionality, which may include or be similar to that provided by the Medtronic CareLink® Network developed by Medtronic plc, of Dublin, Ireland. In some examples, such network technology and functionality may enhance the security of the communications transmitted between the components of FIG. 5, such as the communications transmitted from external device 8 to IMD 4. For example, the network technology and functionality may validate a communication, such as patient or clinician input, transmitted from a device purporting to be external device 8 and directed toward IMD 4, by confirming the identity of the device purporting to be external device 8. In other examples, the network technology and functionality similarly may validate a communication transmitted from another device, such as a device purporting to be one or more of computing devices 150A-150N (e.g., a purported remoter computer located with a clinician) toward IMD 4. In some examples, such security features may protect the cardiac pacing delivered by IMD 4 to the patient from being disrupted, hacked, or otherwise altered by communications originating from unauthorized sources.

In some examples, one or more of computing devices 150A-150N (e.g., device 150A) may be a remote computer, such as a smartphone, tablet or other smart device located with a clinician, by which the clinician may program, receive alerts from, and/or interrogate IMD 4. For example, the clinician may access data pertaining to patient physiological parameters, updated values of CRT parameters, efficacy of delivered CRT, or other data through device 150A, such as when the patient is in in between clinician visits, such as to check on one or more aspects of CRT delivered by IMD 4, as desired. In some examples, the clinician may enter medical instructions for the patient into an application in device 150A, such as an instruction for the patient to schedule a visit with the clinician or for the patient to seek other medical attention, based on data retrieved from IMD 4 by device 150A, or based on other patient data known to the clinician. Device 150A then may transmit the instructions for medical intervention to external device 8, which may help improve clinical outcomes for the patient, such as by helping enable the patient to seek prompt medical intervention.

Figure 6:
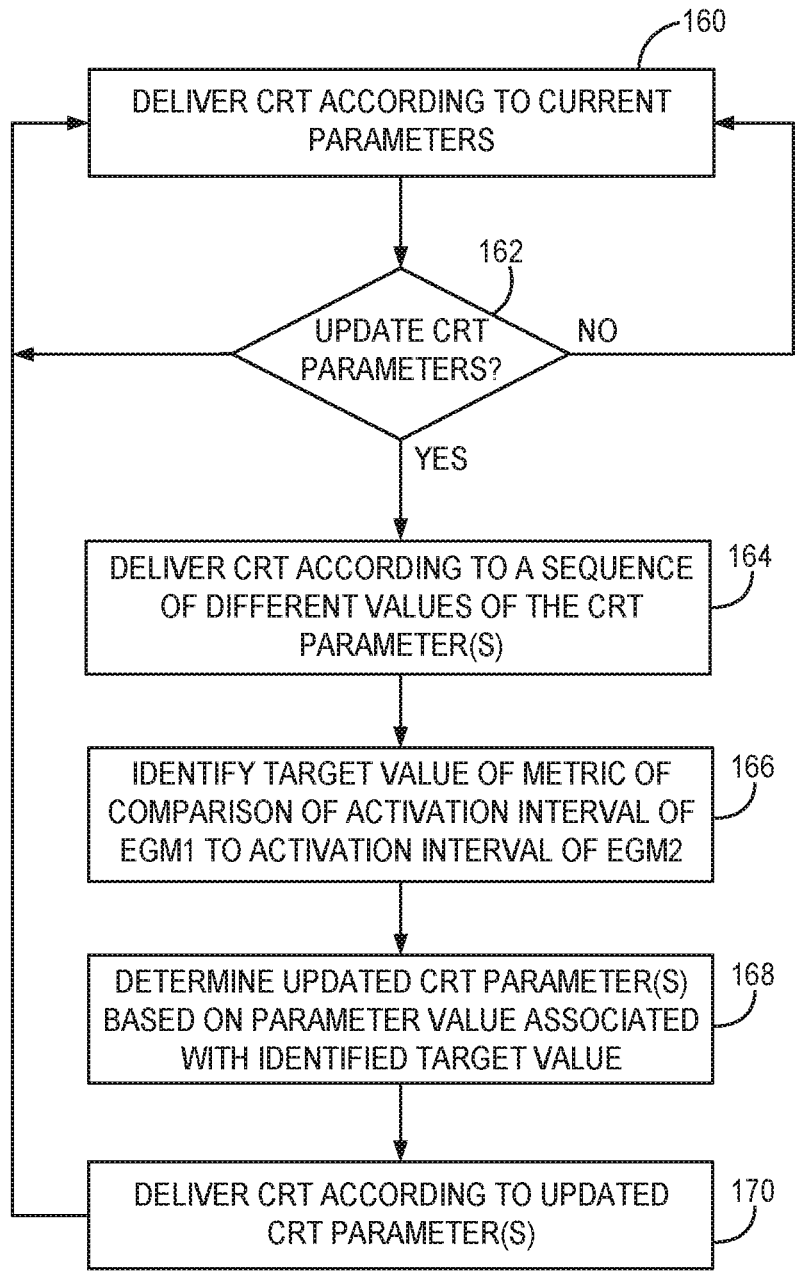
FIG. 6 is a flow diagram illustrating an example technique for updating a CRT parameter and controlling an implantable medical device to deliver CRT according to the updated CRT parameter.

FIG. 6 is a flow diagram illustrating an example technique for updating a CRT parameter and controlling IMD 4 to deliver CRT to heart 6 according to the updated CRT parameter. The CRT parameter may be, for example, an A-V delay or a V-V delay. According to the example of FIG. 6, IMD 4 may deliver CRT (e.g., ventricular pacing) to heart 6 according to a current value of a CRT parameter (160). In some examples, the one or more current values of the CRT parameter may be an initial value by which IMD 4 may deliver CRT to heart 6 as part of a start-up phase following the implantation of IMD 4 within the patient, such as until IMD 4 is prompted to begin automatically updating the value of the CRT parameter by a user, or until an initial post-implantation period of time has elapsed. In other examples, the one or more current values of the one or more CRT parameters may be one or more values determined by processing circuitry 102 during a prior iteration of the technique of FIG. 6. Although one or more steps of the example techniques illustrated in the flow diagrams of FIGS. 6 and 7 may be described as being carried out by processing circuitry 102 of IMD 4, it should be note that such steps alternatively may be carried out by other processing circuitry, such as processing circuitry of external device 8.

During delivery of CRT to heart 6 by IMD 4 according to the current value of the CRT parameter, processing circuitry 102 may determine whether to update the CRT parameters (162). In some examples, processing circuitry 102 may determine whether to update the CRT parameter by determining whether a time period has elapsed. In some examples, the period of time may be on the order of minutes, hours, or days. In other examples, the period of time may be shorter, such as several times per minute or roughly once per cardiac cycle, so as to update the CRT parameter on a nearly continuous or pseudo-continuous basis. In other examples, processing circuitry 102 may determine whether to update the CRT parameter by determining whether a change in a physiological parameter (e.g., a heart rate and/or physical activity level) of the patient has occurred, or by determining whether updating the CRT parameter may be otherwise desirable. In any such examples, if processing circuitry 102 determines that a time period has not elapsed, that a change in a physiological parameter of the patient has not occurred, and/or does not determine that it may be otherwise desirable to update the CRT parameter ("NO" at 162), processing circuitry 102 may continue to control IMD 4 to deliver CRT to heart 6 at the one or more current values of the one or more CRT parameters (160).

If processing circuitry 102 determines that a time period has elapsed, that a change in a physiological parameter of the patient has occurred, and/or determines that it may be otherwise desirable to update the CRT parameter ("YES" at 162), processing circuitry 102 then may control IMD 4 to deliver CRT to heart 6 according to a sequence of different values of the CRT parameter (164). For example, processing circuitry 102 may control IMD 4 to deliver CRT according to a sequence of different values of A-V delay. During delivery of CRT to heart 6 by the IMD according to the sequence of different values of the CRT parameter, processing circuitry 102 may acquire a first electrogram (e.g., "EGM1") and a second electrogram (e.g., "EGM2") from respective ones of a first vector formed from a plurality of electrodes of medical system 2 and a second vector formed from the plurality of electrodes of medical system 2. For example, processing circuitry 102 may acquire a first electrogram and a second electrogram (e.g., electrograms 80 and 82 illustrated in FIGS. 3A and 3B) from respective ones of a first electrode vector and a second electrode vector (e.g., first and second ones of electrode vectors 70, 72, 74, and 76 illustrated in FIG. 2).

Next, processing circuitry 102 may identify a target value of at least one metric of comparison of the first activation interval to the second activation interval (166). In some examples, processing circuitry may determine, for each of the different values of the CRT parameter of the sequence, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram.

As discussed above, the occurrence of the first fiducial may appear in the first electrogram and the second electrogram as a pacing spike. In some other examples, the processing circuitry may determine the timing of the pacing pulse, e.g., based on the time at which the processing circuitry controlled the IMD to deliver the pacing pulse. In some examples, the second fiducial may correspond to a feature of the first electrogram and the second electrogram related to depolarization of the heart in response to a pacing pulse delivered by IMD 4, such as an onset of a paced ventricular activation in the first electrogram and the second electrogram, a maximum dv/dt, a detected R-wave in the first electrogram and the second electrogram, or a maximum amplitude of the first electrogram and the second electrogram. In some examples in which a metric of comparison is at least one of a ratio of the first activation interval to the second activation interval and/or a time difference between the first and second activation intervals, the target value of the metric of comparison may be a minimum value of the time difference (or the ratio value closest to 1), or a value of the time difference that is equal to or less than a threshold value (or a value of the ratio that is within a threshold distance from a value of 1).

In any such examples, the target value may correspond to a desired outcome of delivery of CRT by IMD 4, such as fusion occurring between left ventricular activation and right ventricular activation. Thus, processing circuitry 102 then may determine the updated value of the CRT parameter based on a value of the CRT parameter associated with the identified target value of the metric of comparison (170). Processing circuitry 102 then may control IMD 4 to deliver CRT to heart 6 at the updated value of the CRT parameter to provide CRT to the patient (172). Upon delivery by IMD 4 of CRT to heart 6 at the updated value of the CRT parameter, the updated value of the CRT parameter may be considered a new current value of the CRT parameter (160). The technique of FIG. 6 then may be repeated, in which processing circuitry 102 controls IMD 4 to deliver CRT to heart 6 according to the new current value of the CRT parameter until processing circuitry 102 again determines to update the CRT parameter.

Figure 7:
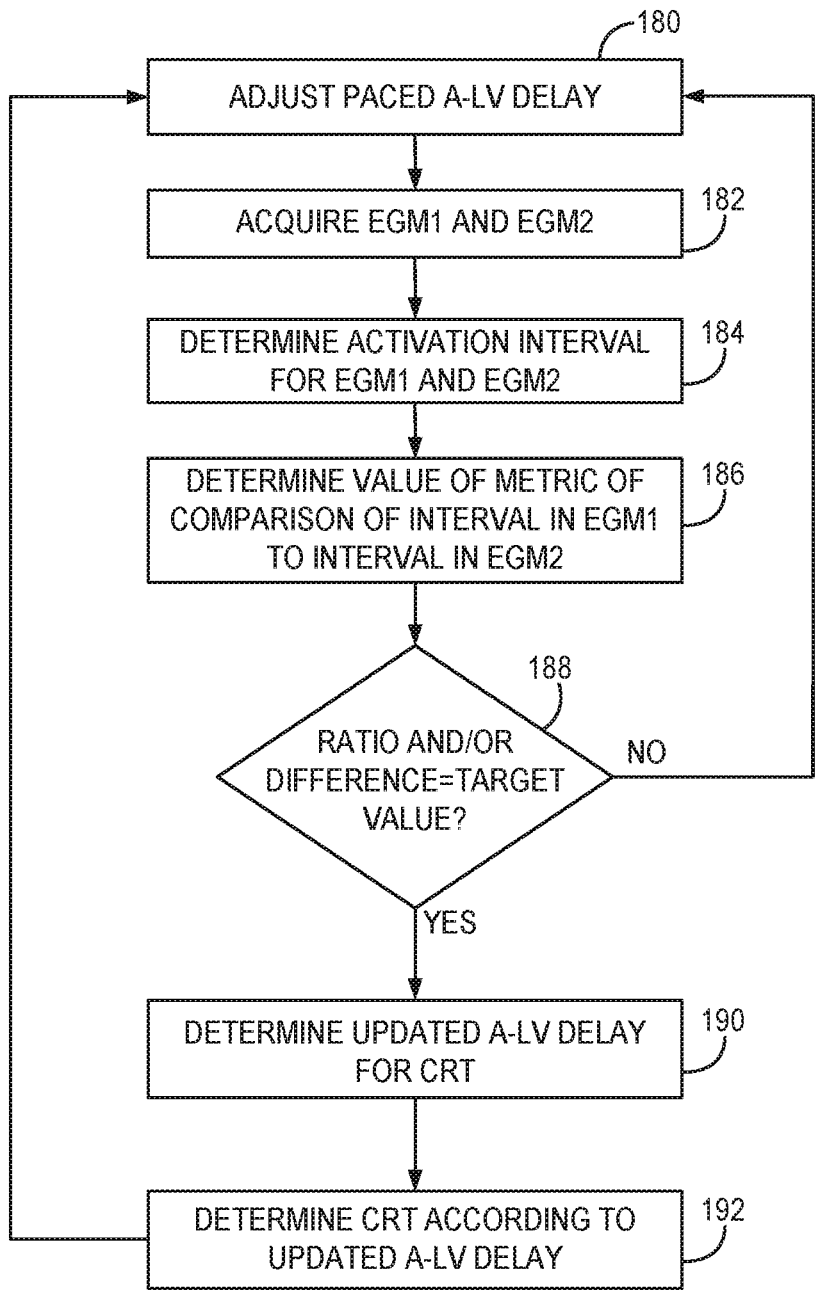
FIG. 7 is a flow diagram illustrating an example technique for updating an A-V delay and controlling an implantable medical device to deliver CRT according to the updated A-V delay.

FIG. 7 is a flow diagram illustrating an example technique for updating an A-LV delay and controlling an implantable medical device to deliver CRT to heart 6 according to the updated A-LV delay. According to the example of FIG. 7, processing circuitry 102 may adjust a paced A-LV delay at which IMD 4 delivers ventricular pacing (e.g., LV fusion pacing) (180). In some examples, processing circuitry 102 may adjust the paced A-LV delay relative to an initial A-LV delay at which IMD 4 may be programmed to deliver ventricular pacing. In other examples, processing circuitry 102 may adjust the paced A-LV delay relative to an updated A-LV delay determined by processing circuitry 102 during a prior iteration of the technique of FIG. 7.

During delivery of CRT to heart 6 by the IMD according to the adjusted paced A-LV delay, processing circuitry 102 may acquire a first electrogram (e.g., "EGM1") and a second electrogram (e.g., "EGM2") from respective ones of a first vector formed from a plurality of electrodes of medical system 2 and a second vector formed from the plurality of electrodes of medical system 2 (182). For example, processing circuitry 102 may acquire a first electrogram and a second electrogram (e.g., electrograms 80 and 82 illustrated in FIGS. 3A and 3B) from respective ones of a first electrode vector and a second electrode vector (e.g., first and second ones of electrode vectors 70, 72, 74, and 76 illustrated in FIG. 2).

Next, processing circuitry 102 may determine a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram (184). In some examples, the first fiducial may correspond to a time at which IMD 4 delivers a pacing pulse during the cardiac cycle. In some examples, the second fiducial may correspond to a feature of the first and second electrograms related to depolarization of the heart in response to the pacing pulse, such as one of an onset of a paced ventricular activation in EGM1 and EGM2, such as one of an onset of a paced ventricular activation in EGM1 and EGM2, a maximum dv/dt, a detected R-wave in EGM1 and EGM2, or a maximum amplitude of EGM1 and EGM2. In some examples in which the metric of comparison is at least one of a ratio of the first activation interval to the second activation interval and/or a time difference between the first and second activation intervals, the target value of the metric of comparison may be a minimum value of the time difference (or the ratio value closest to 1), or a value of the time difference that is equal to or less than a threshold value (or a value of the ratio that is within a threshold distance from a value of 1).

Next, processing circuitry 102 may determine a value of at least one a metric of comparison of the first activation interval to the second activation interval (186) and determine whether a value of the at least one a metric of comparison is a target value of the at least one a metric of comparison (188). In any such examples, the target value may correspond to a desired outcome of delivery of CRT to heart 6 by IMD 4, such as fusion occurring between left ventricular activation and right ventricular activation.

If processing circuitry 102 determines that the value of the at least one metric of comparison is not the target value ("NO" at 188), processing circuitry 102 may adjust the paced A-LV delay and control IMD 4 to deliver CRT to heart 6 according to the new adjusted paced A-LV delay (180). If processing circuitry 102 determines that the value of the at least one metric of comparison is the target value ("YES" at 188), processing circuitry 102 then may determine an updated A-LV delay at which to control IMD 4 to deliver CRT to heart 6 (190). For example, the updated A-LV delay may be the adjusted paced A-LV delay at which IMD 4 delivered CRT to heart 6 at (180).

Processing circuitry 102 then may control IMD 4 to deliver CRT to heart 6 at the updated A-LV delay to provide CRT (192). Processing circuitry 102 may control IMD 4 to deliver CRT to heart 6 at the updated A-LV delay to provide CRT until determines that a time period has elapsed, that a change in a physiological parameter of the patient has occurred, and/or determines that it may be otherwise desirable to again update the A-LV delay. The technique of FIG. 7 then may be repeated, in which processing circuitry 102 again adjusts the A-LV delay and controls IMD 4 to deliver CRT to heart 6 according to the new adjusted paced A-LV delay (180).

In this manner, the example technique of FIG. 6 and/or the example technique of FIG. 7 may enable ongoing (e.g., periodic or substantially continuous), ambulatory determination of updated (e.g., patient-specific) values of one or more CRT parameters by processing circuitry 102 based on first and second electrograms acquired from first and second electrode vectors formed from a plurality of electrodes of system 2, instead of infrequent determinations of an updated value of a CRT parameter made in a clinician's office or hospital. In some examples, the techniques of FIGS. 6 and/or 7 may improve acute hemodynamic benefits of CRT and/or may improve short-term clinical response. In some examples, such an improvement in hemodynamic benefit and/or short-term clinical response may improve symptoms experienced by the patient, such as examples in which the patient otherwise does not obtain significant clinical benefit from CRT.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

In addition, the functions and techniques described in this disclosure may be provided by a medical device system that includes a plurality of IMDs. In some such examples, an IMD that may be controlled by processing circuitry to deliver ventricular pacing may not include the sensing electrodes by which the processing circuitry acquires electrograms. For example, some such medical device systems may include a leaded IMD that includes one or more intravascular leads or an extravascular ICD may include electrodes that form the first and second electrode vectors in combination with an LPD configured to be placed on or within the left ventricle and deliver ventricular pacing thereto.

In some such examples, processing circuitry of the medical device system (e.g., processing circuitry of the leaded IMD or extravascular IMD) may control the LPD to deliver ventricular pacing at a series of A-LV delays. The leaded IMD or extravascular IMD may detect pacing pulses delivered by LPD and the resulting ventricular activation in electrodes acquired by the processing circuitry from the first and second electrode vectors. The processing circuitry then may determine an updated value of a CRT parameter according to the techniques described herein and control the LPD to deliver LV pacing at the updated value of the CRT parameter to provide CRT.

Various aspects of the disclosure have been described. These and other aspects are within the scope of the following claims.

The invention claimed is:

1. A method for controlling delivery of cardiac resynchronization therapy (CRT) using an implantable medical device configured for implantation within a patient, the method comprising, by processing circuitry of a medical device system comprising the implantable medical device:

controlling the implantable medical device to deliver ventricular pacing to a heart of the patient according to a sequence of different values of a CRT parameter;

acquiring, during the delivery of ventricular pacing according to the sequence, a first electrogram and a second electrogram from respective ones of a first vector formed from a plurality of electrodes of the medical device system and a second vector formed from the plurality of electrodes;

determining, for each of the different values of the CRT parameter, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram;

determining, for each of the different values of the CRT parameter, a value of a metric of comparison of the first activation interval to the second activation interval, wherein the metric of comparison comprises one or more of a ratio of the first and second activation intervals and a time difference between the first and second activation intervals;
determining an updated value of the CRT parameter using the metric of comparison and a target value; and
controlling the implantable medical device to deliver the ventricular pacing with the updated value of the CRT parameter.

2. The method of claim 1, wherein the target value corresponds to fusion occurring between left ventricular activation and right ventricular activation.

3. The method of claim 1, wherein the time difference is a time difference between the occurrence of the second fiducial of the cardiac cycle detected in the first electrogram and the occurrence of the second fiducial of the cardiac cycle detected in the second electrogram, and wherein the method further comprises identifying the target value of the metric of comparison comprises identifying a minimum value of the time difference.

4. The method of claim 1, wherein the target value comprises one of a minimum value of the time difference or a value of the ratio that is closest to a value of 1.

5. The method of claim 1, wherein the target value comprises one of a value of the one or more of the ratio or the time difference that is equal to or less than a threshold value or a value of the ratio that is within a threshold distance from a value of 1.

6. The method of claim 1, wherein the CRT parameter is an A-V delay.

7. The method of claim 1, wherein the CRT parameter is a V-V delay.

8. The method of claim 1, wherein the CRT parameter comprises an atrioventricular (A-V) delay, wherein controlling the implantable medical device to deliver ventricular pacing according to a sequence of different values of a CRT parameter comprises controlling the implantable medical device to deliver left-ventricular pacing according to a sequence of different values of A-V delay, and wherein controlling the implantable medical device to deliver the ventricular pacing with the updated value of the CRT parameter comprises controlling the implantable medical device to deliver left ventricular fusion pacing.

9. The method of claim 1, wherein controlling the implantable medical device to deliver the ventricular pacing at the updated value of the CRT parameter comprises controlling the implantable medical device to deliver the ventricular pacing at the value of the CRT parameter that resulted in the target value.

10. The method of claim 1, wherein the first fiducial corresponds to a time of delivery by the implantable medical device of a ventricular pacing pulse for the cardiac cycle.

11. The method of claim 1, wherein the second fiducial corresponds to one of onset of a paced ventricular activation, a maximum dv/dt, a detected R-wave, and a maximum amplitude of the first electrogram and the second electrogram.

12. The method of claim 1, wherein the first vector and the second vector are orthogonal to one another.

13. The method of claim 1, wherein the first vector and the second vector each include a common electrode of the plurality of electrodes.

14. The method of claim 1, wherein the implantable medical device comprises an implantable CRT device comprising the processing circuitry, wherein the implantable CRT device is coupled to the plurality of electrodes by one or more implantable leads configured for implantation within the patient, each of the one or more implantable leads comprising one or more electrodes of the plurality of electrodes.

15. The method of claim 14, wherein the implantable CRT device comprises a housing comprising an electrode of the plurality of electrodes and the one or more implantable leads comprises a first lead configured for implantation within a right ventricle of the heart and a second lead configured for implantation within a left ventricle of the heart, wherein the first vector is between the housing and at least one electrode of the one or more electrodes on the first lead, and wherein the second vector is between at least one electrode of the one or more electrodes on the first lead and at least one electrode of the one or more electrodes on the second lead.

16. The method of claim 1, wherein the medical device system further comprises a memory and wherein controlling the implantable medical device to deliver the ventricular pacing to the heart of the patient according to the sequence of different values of the CRT parameter comprises controlling the implantable medical device to deliver the ventricular pacing to the heart of the patient according to the sequence of different values of the CRT parameter based on a determination to update one or more CRT parameters, the one or more CRT parameters comprising the CRT parameter, the method further comprising storing the updated CRT parameter in the memory as at least one updated value of the one or more CRT parameters.

17. The method of claim 1, wherein determining an updated value of the CRT parameter using the metric of comparison and a target value comprises determining the updated value of the CRT parameter based upon a comparison of the metric of comparison to the target value.

18. The method according to claim 17, wherein determining the updated value of the CRT parameter based upon a comparison of the metric of comparison to the target value comprises determining which one of the different values of the CRT parameter is closest to the target value and selecting the value of the CRT parameter that is closest to the target value as the updated value of the CRT parameter.

19. A system for controlling delivery of cardiac resynchronization therapy (CRT) to a patient, the system comprising:
a plurality of electrodes;
an implantable medical device configured to deliver ventricular pacing to the patient;
sensing circuitry configured to sense electrical activity of the heart via the plurality of electrodes; and
processing circuitry configured to:
control the implantable medical device to deliver ventricular pacing according to a sequence of different values of a CRT parameter;
acquire, via the sensing circuitry and during the delivery of ventricular pacing according to the sequence, a first electrogram and a second electrogram from respective ones of a first vector formed from the plurality of electrodes and a second vector formed from the plurality of electrodes;
determine, for each of the different values of the CRT parameter, a first activation interval between an occurrence of a first fiducial of a cardiac cycle and a second fiducial of a cardiac cycle detected in the first electrogram and a second activation interval between the occurrence of the first fiducial of the cardiac cycle and the second fiducial of a cardiac cycle detected in the second electrogram;

determine, for each of the different values of the CRT parameter, a value of a metric of comparison of the first activation interval to the second activation interval, wherein the metric of comparison comprises one or more of a ratio of the first and second activation intervals and a time difference between the first and second activation intervals;

determine an updated value of the CRT parameter using the metric of comparison; and control the implantable medical device to deliver the ventricular pacing with the updated value of the CRT parameter.

20. A system according to claim 19, wherein the processing circuitry is configured to determine the updated value of the CRT parameter based upon a comparison of the metric of comparison to a defined target value.

21. A system according to claim 20, wherein the processing circuitry is further configured to determine which one of the different values of the CRT parameter is closest to the target value and select the value of the CRT parameter that is closest to the target value as the updated value of the CRT parameter.

22. The system of claim 20, wherein the target value corresponds to fusion occurring between left ventricular activation and right ventricular activation.

23. The system of claim 20, wherein the time difference is a time difference between the occurrence of the second fiducial of the cardiac cycle detected in the first electrogram and the occurrence of the second fiducial of the cardiac cycle detected in the second electrogram, and wherein the processing circuitry is further configured to identify the target value of the metric of comparison by identifying a minimum value of the time difference.

24. The system of claim 20, wherein the target value comprises one of a minimum value of the time difference and a value of the ratio that is closest to a value of 1.

25. The system of claim 20, wherein the target value comprises one of a value of the one or more of the ratio and the time difference that is equal to or less than a threshold value or a value of the ratio that is within a threshold distance from a value of 1.

26. The system of claim 19, wherein the CRT parameter is an A-V delay.

27. The system of claim 19, wherein the CRT parameter is a V-V delay.

28. The system of claim 19, wherein the CRT parameter comprises an atrioventricular (A-V) delay, wherein controlling the implantable medical device to deliver ventricular pacing according to a sequence of different values of a CRT parameter comprises controlling the implantable medical device to deliver ventricular pacing according to a sequence of different values of the A-V delay, and wherein controlling the implantable medical device to deliver the ventricular pacing with the updated value of the CRT parameter comprises controlling the implantable medical device to deliver left ventricular fusion pacing.

29. The system of claim 20, wherein the processing circuitry is configured to control the implantable medical device to deliver the ventricular pacing with the updated value of the CRT parameter by at least controlling the implantable medical device to deliver the ventricular pacing at the value of the CRT parameter that resulted in the target value.

30. The system of claim 19, wherein the first fiducial corresponds to a time of delivery by the implantable medical device of a ventricular pacing pulse for the cardiac cycle.

31. The system of claim 19, wherein the second fiducial corresponds to one of onset of a paced ventricular activation, a maximum dv/dt, a detected R-wave, and a maximum amplitude of the first electrogram and the second electrogram.

32. The system of claim 19, wherein the first vector and the second vector are orthogonal to one another.

33. The system of claim 19, wherein the first vector and the second vector each include a common electrode of the plurality of electrodes.

34. The system of claim 19, wherein the implantable medical device comprises an implantable CRT device comprising the processing circuitry, the system further comprising one or more implantable leads configured for implantation within the patient, wherein the implantable CRT device is coupled to the plurality of electrodes by the one or more implantable leads, each of the one or more implantable leads comprising one or more electrodes of the plurality of electrodes.

35. The system of claim 34, wherein the implantable CRT device further comprises a housing comprising an electrode of the plurality of electrodes and the one or more implantable leads comprises a first lead configured for implantation within a right ventricle of the heart and a second lead configured for implantation within a left ventricle of the heart, wherein the first vector is between the housing and at least one electrode of the one or more electrodes on the first lead, and wherein the second vector is between at least one electrode of the one or more electrodes on the first lead and at least one electrode of the one or more electrodes on the second lead.

36. The system of claim 19, wherein the medical device system further comprises a memory and the processing circuitry is configured to control the implantable medical device to deliver the ventricular pacing to the heart of the patient according to the sequence of different values of the CRT parameter by at least controlling the implantable medical device to deliver the ventricular pacing to the heart of the patient according to the sequence of different values of the CRT parameter based on a determination to update one or more CRT parameters, the one or more CRT parameters comprising the CRT parameter, and wherein the processing circuitry is further configured to store the updated CRT parameter in the memory as at least one updated value of the one or more CRT parameters.

37. A system for controlling delivery of cardiac resynchronization therapy (CRT) to a patient, the system comprising:

a plurality of electrodes;

an implantable medical device configured to deliver ventricular pacing to the patient;

sensing circuitry configured to sense electrical activity of the heart via the plurality of electrodes; and processing circuitry configured to:
control the implantable medical device to deliver ventricular pacing according to a sequence of different values of an A-V delay;

acquire, via the sensing circuitry and during the delivery of ventricular pacing according to the sequence, a first electrogram and a second electrogram from respective ones of a first vector formed from the plurality of electrodes and a second vector formed from the plurality of electrodes;

determine, for each of the different values of the A-V delay, a first activation interval between an occurrence of a first fiducial of a cardiac cycle and a second fiducial of the cardiac cycle detected in the first electrogram and a second activation interval between the occurrence of the first fiducial of the cardiac cycle and the second fiducial of the cardiac cycle detected in the second electrogram;

determine, for each of the different values of the A-V delay, one or more of a ratio of the first activation interval and the second activation interval and a time difference between the first activation interval and the second activation interval;

identify one or more of a minimum value of the time difference and a value of the ratio that is closest to a value of 1;

determine an updated value of the A-V delay based on the identified one or more of the minimum value of the time delay and the value of the ratio that is closest to a value of 1; and control the implantable medical device to deliver the ventricular pacing with the updated value of the A-V delay to provide CRT.

38. A non-transitory computer-readable medium storing instructions for causing processing circuitry to perform a method for controlling delivery of cardiac resynchronization therapy (CRT) using a medical device system, the medical device system comprising the processing circuitry, a plurality of electrodes, an implantable medical device configured for implantation within a patient and comprising at least one electrode of the plurality of electrodes, and sensing circuitry configured to sense electrical activity of the heart via the plurality of electrodes, the method comprising:

controlling the implantable medical device to deliver ventricular pacing according to a sequence of different values of a CRT parameter;

acquiring, during the delivery of ventricular pacing according to the sequence, a first electrogram and a second electrogram from respective ones of a first vector formed from the plurality of electrodes and a second vector formed from the plurality of electrodes;

determining, for each of the different values of the CRT parameter, a first activation interval between an occurrence of a first fiducial of a cardiac cycle and a second fiducial of the cardiac cycle determined in the first electrogram and a second activation interval between the occurrence of the first fiducial of the cardiac cycle and the second fiducial of the cardiac cycle determined in the second electrogram;

determining, for each of the different values of the CRT parameter, a value of a metric of comparison of the first activation interval to the second activation interval;

identifying a target value of the metric of comparison of the first activation interval to the second activation interval;

determining an updated value of the CRT parameter based on the identified target value; and controlling the implantable medical device to deliver the ventricular pacing at the updated value of the CRT parameter to provide CRT.

39. The non-transitory computer-readable medium of claim 38, wherein the metric of comparison comprises one or more of a ratio of the first activation interval to the second activation interval and a time difference between the first activation interval and the second activation interval.

40. The non-transitory computer-readable medium of claim 39, wherein the time difference is a time difference between the occurrence of the second fiducial of the cardiac cycle detected in the first electrogram and the occurrence of the second fiducial of the cardiac cycle detected in the second electrogram, and wherein identifying the target value of the metric of comparison comprises identifying a minimum value of the time difference.

41. The non-transitory computer-readable medium of claim 39, wherein the target value comprises one of a minimum value of the time difference and a value of the ratio that is closest to a value of 1.

42. The non-transitory computer-readable medium of claim 39, wherein the target value comprises one of a value of the one or more of the ratio and the time difference that is equal to or less than a threshold value or a value of the ratio that is within a threshold distance from a value of 1.

43. The non-transitory computer-readable medium of any of claims 38-42, wherein the first vector and the second vector are orthogonal to one another.

* * * * *